United States Patent
Gil et al.

(10) Patent No.: US 10,238,326 B2
(45) Date of Patent: Mar. 26, 2019

(54) FLUSHABLE FLUID HANDLING ASSEMBLY

(71) Applicant: Elcam Medical Agricultural cooperative association LTD, Kibbutz Bar-am (IL)

(72) Inventors: Tomer Gil, Mizpe Hila (IL); Alex Zislin, Nahariya (IL)

(73) Assignee: Elcam Medical Agricultural Cooperative Association Ltd., Kibbutz Bar-am (IL)

( * ) Notice: Subject to any disclaimer, the term of this patent is extended or adjusted under 35 U.S.C. 154(b) by 366 days.

(21) Appl. No.: 15/228,175

(22) Filed: Aug. 4, 2016

(65) Prior Publication Data

US 2018/0035937 A1    Feb. 8, 2018

(51) Int. Cl.
*A61B 5/15* (2006.01)
*A61M 39/22* (2006.01)

(52) U.S. Cl.
CPC .... *A61B 5/150992* (2013.01); *A61B 5/15003* (2013.01); *A61B 5/150221* (2013.01); *A61B 5/150236* (2013.01); *A61M 39/223* (2013.01); *A61M 2039/229* (2013.01)

(58) Field of Classification Search
CPC ........ A61B 15/150992; A61B 5/15003; A61B 5/150221; A61B 5/15101; A61B 5/15103; A61B 5/15105; A61B 5/15107; A61B 5/15109; A61B 5/15111; A61B 5/15113; A61M 39/223; A61M 2039/229
See application file for complete search history.

(56) References Cited

U.S. PATENT DOCUMENTS

| | | | |
|---|---|---|---|
| 2,868,176 A | 1/1959 | Bennett |
| 3,721,265 A | 3/1973 | Hoffland |
| 3,780,736 A | 12/1973 | Chen |
| 3,834,372 A | 9/1974 | Turney |
| 4,146,055 A | 3/1979 | Ryder |
| 4,397,335 A | 8/1983 | Doblar |
| 4,608,996 A | 9/1986 | Brown |
| 4,654,027 A | 3/1987 | Dragan |
| 4,697,797 A | 10/1987 | Gold |

(Continued)

FOREIGN PATENT DOCUMENTS

| | | |
|---|---|---|
| EP | 1234596 A1 | 6/2001 |
| EP | 1426604 B1 | 6/2004 |

(Continued)

*Primary Examiner* — Philip R Wiest
(74) *Attorney, Agent, or Firm* — Fish & Richardson P.C.

(57) ABSTRACT

A flushable fluid handling assembly including a housing element defining a central bore and at least first, second and third ports, the first and third ports being line connection ports and the second port being a syringe connection port, a handle element which is selectably positionable relative to the housing element, at least one fluid passageway communicating between at least two of the at least first, second and third ports, the at least one fluid passageway being selectably defined by rotational positioning of the handle element relative to the housing element, a first fluid flow guide extending radially to an inner facing wall of the central bore, the first fluid flow guide associated with the at least one fluid flow passageway and a syringe fixedly connected to the second port, the syringe including an axially displaceable plunger.

28 Claims, 24 Drawing Sheets

(56) References Cited

U.S. PATENT DOCUMENTS

| | | | |
|---|---|---|---|
| 4,967,797 | A | 11/1990 | Manska |
| 5,002,066 | A | 3/1991 | Simpson |
| 5,105,853 | A | 4/1992 | Lie |
| 5,135,026 | A | 8/1992 | Manska |
| 5,340,364 | A | 8/1994 | Ghelli |
| 5,340,634 | A | 8/1994 | Adams |
| 5,466,228 | A | 11/1995 | Evans |
| 5,549,651 | A | 8/1996 | Lynn |
| 5,578,016 | A | 11/1996 | Zinger |
| 6,036,171 | A | 3/2000 | Weinheimer |
| 6,089,541 | A | 7/2000 | Weinheimer |
| 6,238,372 | B1 | 5/2001 | Zinger |
| RE37,357 | E | 9/2001 | Lynn |
| 6,651,956 | B2 | 11/2003 | Miller |
| 6,780,736 | B1 | 8/2004 | Holmes |
| 6,864,372 | B2 | 3/2005 | Kano |
| 7,186,236 | B2 | 3/2007 | Gibson |
| 7,232,428 | B1 | 6/2007 | Inukai |
| 7,470,261 | B2 | 12/2008 | Lynn |
| 7,520,489 | B2 | 4/2009 | Ruschke |
| 7,695,445 | B2 | 4/2010 | Yuki |
| 7,984,730 | B2 * | 7/2011 | Ziv ............... A61M 39/223 137/239 |
| 8,534,321 | B2 | 9/2013 | Ziv |
| 2004/0210162 | A1 | 10/2004 | Wyatt |
| 2011/0308651 | A1 | 12/2011 | Ziv |

FOREIGN PATENT DOCUMENTS

| | | |
|---|---|---|
| JP | 11342209 | 12/1999 |
| JP | 2003159336 A | 12/2004 |
| JP | 5415073 B2 | 9/2006 |
| JP | 2002153562 | 10/2007 |
| WO | 2006025054 A3 | 3/2006 |
| WO | 2007033319 A1 | 3/2007 |

* cited by examiner

FLUSHABLE FLUID HANDLING ASSEMBLY

REFERENCE TO RELATED PATENT APPLICATIONS AND PATENTS

Reference is hereby made to U.S. Pat. Nos. 7,984,730; 8,534,321; 9,016,316 and pending U.S. patent application Ser. No. 14/665,850, which has been published as U.S. Patent Publication No. 2015/0196749, the disclosures of which are hereby incorporated by reference.

FIELD OF THE INVENTION

The present invention relates to fluid handling assemblies and methods, particularly suitable for medical applications.

BACKGROUND OF THE INVENTION

Various types of fluid handling devices are known in the art. A particularly suitable fluid handling device is described in U.S. Pat. Nos. 7,984,730; 8,534,321; 9,016,316 and pending U.S. patent application Ser. No. 14/665,850, which has been published as U.S. Patent Publication No. 2015/0196749, of the present assignee.

SUMMARY OF THE INVENTION

The present invention seeks to provide an improved fluid handling assembly and method, particularly suitable for blood sampling.

There is thus provided in accordance with a preferred embodiment of the present invention a flushable fluid handling assembly including a housing element defining a central bore and at least first, second and third ports, the first and third ports being line connection ports and the second port being a syringe connection port, a handle element which is selectably positionable relative to the housing element, at least one fluid passageway communicating between at least two of the at least first, second and third ports, the at least one fluid passageway being selectably defined by rotational positioning of the handle element relative to the housing element, a first fluid flow guide extending radially to an inner facing wall of the central bore, the first fluid flow guide associated with the at least one fluid flow passageway and a syringe fixedly connected to the second port, the syringe including an axially displaceable plunger.

Preferably, the flushable fluid handling assembly also includes a second fluid flow guide extending radially and partially bifurcating the second port, the second fluid flow guide being associated with the at least one fluid flow passageway.

In accordance with a preferred embodiment of the present invention the syringe has a luer connector having an interior volume and the second port is sealingly threadably connected to the luer connector. Additionally, the at least one fluid passageway is configured for enabling flushing of at least one of the interior volume of the luer connector and the second port by a fluid flow which does not flow entirely through said second port whose internal volume is being flushed.

Preferably, the first fluid flow guide and the second fluid flow guide are configured to be selectively arranged along a single axis for enabling flushing of at least one of the interior volume and the second port.

In accordance with a preferred embodiment of the present invention the handle element and the housing element are arrangeable in multiple mutual positions, and the first fluid flow guide and the at least one fluid passageway are configured for enabling flushing at least one of the second port and the interior volume by a fluid flow which does not flow entirely through said second port whose internal volume is being flushed when the housing element and the handle element are in at least one of the multiple mutual positions. Alternatively, the handle element and the housing element are arrangeable in multiple mutual positions and the first fluid flow guide, the second fluid flow guide, which is selectively arranged along a single axis with the first fluid flow guide, and the at least one fluid passageway are configured for enabling flushing at least one of the second port and the interior volume by a fluid flow which does not flow entirely through said second port whose internal volume is being flushed when the housing element and the handle element are in at least one of the multiple mutual positions.

Preferably, the syringe is adapted for use in a blood sampling procedure. Additionally, the syringe is adapted to serve as a container for diluted blood being present in the flushable fluid handling assembly as part of the blood sampling procedure.

In accordance with a preferred embodiment of the present invention the flushable fluid handling assembly also includes a mounting base and the syringe is snap-fit mounted onto the mounting base. Additionally, the housing element is snap-fit mounted onto the mounting base.

In accordance with a preferred embodiment of the present invention the handle element and the syringe are positionable in at least one of the following operative orientations: a first operative orientation in which the handle element is positioned so as to provide fluid communication along at least part of the at least one fluid passageway between the first, second and third ports and the plunger of the syringe is in an extended position and the passageway is filled with a first fluid, a second operative orientation in which the handle element is positioned so as to provide fluid communication along at least part of the at least one fluid passageway only between the first and third ports, a third operative orientation in which the handle element is positioned so as to provide fluid communication along at least part of the at least one fluid passageway between the second and third ports, a fourth operative orientation in which the handle element is positioned so as to provide fluid communication along at least part of the at least one fluid passageway between the second and third ports and the plunger of the syringe is in a retracted position, thereby drawing a second fluid via the third port into at least part of the passageway, the second port and the syringe, a fifth operative orientation in which the handle element is positioned so as to provide fluid communication along at least part of the at least one fluid passageway between the first and second ports but not with the third port and the plunger remains retracted, thereby preventing the first fluid from passing through the third port, a sixth operative orientation in which the handle element is positioned so as to provide fluid communication along at least part of the at least one fluid passageway between the second and third ports and the plunger is extended, thereby forcing the second fluid out of the syringe, the internal volume and the at least one fluid passageway via the third port, a seventh operative orientation in which the handle element is positioned so as to provide fluid communication along at least part of the at least one fluid passageway between the first, second and third ports and the plunger of the syringe is in a retracted position, an eighth operative orientation in which the handle element is positioned so as to provide fluid communication along at least part of the at least one fluid passageway between the first, second and third ports and the plunger is extended, thereby flushing the second fluid from the second port and the at least one fluid passageway.

Preferably, the first fluid is saline and the second fluid is a diluted blood.

In accordance with a preferred embodiment of the present invention at least one of the operative orientations is useful for at least one of the following operations: priming of the flushable fluid handling assembly, blood pressure monitoring via a blood pressure transducer forming part of the flushable fluid handling assembly, drawing a blood sample from a patient causing the diluted blood to be drawn into the syringe, isolating the blood sample from the at least one fluid passageway and from the syringe, sampling blood from the flushable fluid handling assembly, directing the blood sample and the diluted blood back to the patient from the fluid passageway and from the syringe and flushing of the second port, the at least one fluid passageway and the syringe.

There is also provided in accordance with another preferred embodiment of the present invention a method of blood sampling using a flushable fluid handling assembly, including the steps of providing a stopcock fixedly connected to a syringe having a displaceable plunger and a luer connector defining an interior volume, the stopcock being adapted to be fluidly coupled to an IV line, which is connected to an IV bag containing a first fluid, the stopcock including a housing element, a handle element, at least one fluid flow passageway defined by relative arrangement between the housing element and the handle element and a fluid flow guide associated with the fluid flow passageway, providing a blood sampling port, fluidly coupled to the IV line, to the stopcock and to a patient circulatory system and located between the stopcock and the patient, filling the IV line with the first fluid, drawing a second fluid from the patient into at least part of the IV line, by displacing the displaceable plunger of the syringe, sampling the second fluid using the blood sampling port, directing the second fluid back into the patient, by displacing the displaceable plunger of the syringe and flushing the interior volume of the luer connector by a fluid flow of the first fluid flowing past the fluid flow guide.

Preferably, the housing element defines a central bore and at least first, second and third ports, the first and third ports being line connection ports and the second port being a syringe connection port, the handle element is selectably positionable relative to the housing element, the fluid flow passageway communicates between at least two of the at least first, second and third ports, the at least one fluid flow passageway being selectably defined by rotational positioning of the handle element relative to the housing element and the first fluid flow guide extends radially to an inner facing wall of the central bore, the first fluid flow guide associated with the at least one fluid flow passageway. Additionally, the stopcock also includes a second fluid flow guide extending radially and partially bifurcating the second port, the second fluid flow guide being associated with the at least one fluid flow passageway.

In accordance with a preferred embodiment of the present invention the second port is sealingly threadably connected to the luer connector of the syringe. Additionally or alternatively, the at least one fluid passageway is configured for enabling flushing at least one of the interior volume of the luer connector and the second port by a fluid flow which does not flow entirely through said second port whose internal volume is being flushed. Additionally or alternatively, the first fluid flow guide and the second fluid flow guide are configured to be selectively arranged along a single axis for enabling flushing of at least one of the interior volume and the second port.

Preferably, the handle element and the housing element are arrangeable in multiple mutual positions and the first fluid flow guide and the at least one fluid passageway are configured for enabling flushing of at least one of the second port and the interior volume by a fluid flow which does not flow entirely through said second port whose internal volume is being flushed when the housing element and the handle element are in at least one of the multiple mutual positions. Alternatively, the handle element and the housing element are arrangeable in multiple mutual positions and the first fluid flow guide, the second fluid flow guide, which is selectively arranged along a single axis with the first fluid flow guide, and the at least one fluid passageway are configured for enabling flushing at least one of the second port and the interior volume by a fluid flow which does not flow entirely through said second port whose internal volume is being flushed when the housing element and the handle element are in at least one of the multiple mutual positions.

In accordance with a preferred embodiment of the present invention the providing also includes providing a mounting base and the syringe is snap-fit mounted onto the mounting base. Additionally, the housing element is snap-fit mounted onto the mounting base.

Preferably, the handle element and the first syringe are positionable in at least one of the following operative orientations: a first operative orientation in which the handle element is positioned so as to provide fluid communication along at least part of the at least one fluid passageway between the first, second and third ports and the first plunger of the first syringe is in an extended position and the passageway is filled with a first fluid, a second operative orientation in which the handle element is positioned so as to provide fluid communication along at least part of the at least one fluid passageway only between the first and third ports, a third operative orientation in which the handle element is positioned so as to provide fluid communication along at least part of the at least one fluid passageway between the second and third ports, a fourth operative orientation in which the handle element is positioned so as to provide fluid communication along at least part of the at least one fluid passageway between the second and third ports and the first plunger of the first syringe is in a retracted position, thereby drawing a second fluid via the third port into at least part of the passageway, the second port and the syringe, a fifth operative orientation in which the handle element is positioned so as to provide fluid communication along at least part of the at least one fluid passageway between the first and second ports but not with the third port and the first plunger remains retracted, thereby preventing the first fluid from passing through the third port, a sixth operative orientation in which the handle element is positioned so as to provide fluid communication along at least part of the at least one fluid passageway between the second and third ports and the first plunger is extended, thereby forcing the second fluid out of the syringe, the internal volume and the at least one fluid passageway via the third port, a seventh operative orientation in which the handle element is positioned so as to provide fluid communication along at least part of the at least one fluid passageway between the first, second and third ports and the plunger of the syringe is in a retracted position and an eighth operative orientation in which the handle element is positioned so as to provide fluid communication along at least part of the at least one fluid passageway between the first, second and third ports and the first plunger is extended, thereby flushing the second fluid from the second port and the at least one fluid passageway.

In accordance with a preferred embodiment of the present invention the first fluid is saline and the second fluid is a diluted blood.

In accordance with a preferred embodiment of the present invention at least one of the operative orientations is useful for at least one of the following operations: priming of the flushable fluid handling assembly, blood pressure monitoring via a blood pressure transducer forming part of the flushable fluid handling assembly, drawing a blood sample from a patient causing the diluted blood to be drawn into the syringe, isolating the blood sample from the at least one fluid passageway and from the syringe, sampling blood from the flushable fluid handling assembly, directing the blood sample and the diluted blood back to the patient from the fluid passageway and from the syringe and flushing of the second port, the at least one fluid passageway and the syringe.

Preferably, the syringe is adapted to serve as a container for the diluted blood being present in the flushable fluid handling assembly as part of the blood sampling procedure.

BRIEF DESCRIPTION OF THE DRAWINGS

The present invention will be understood and appreciated more fully from the following detailed description, taken in conjunction with the drawings in which.

DETAILED DESCRIPTION OF PREFERRED EMBODIMENTS

Figure 1A:
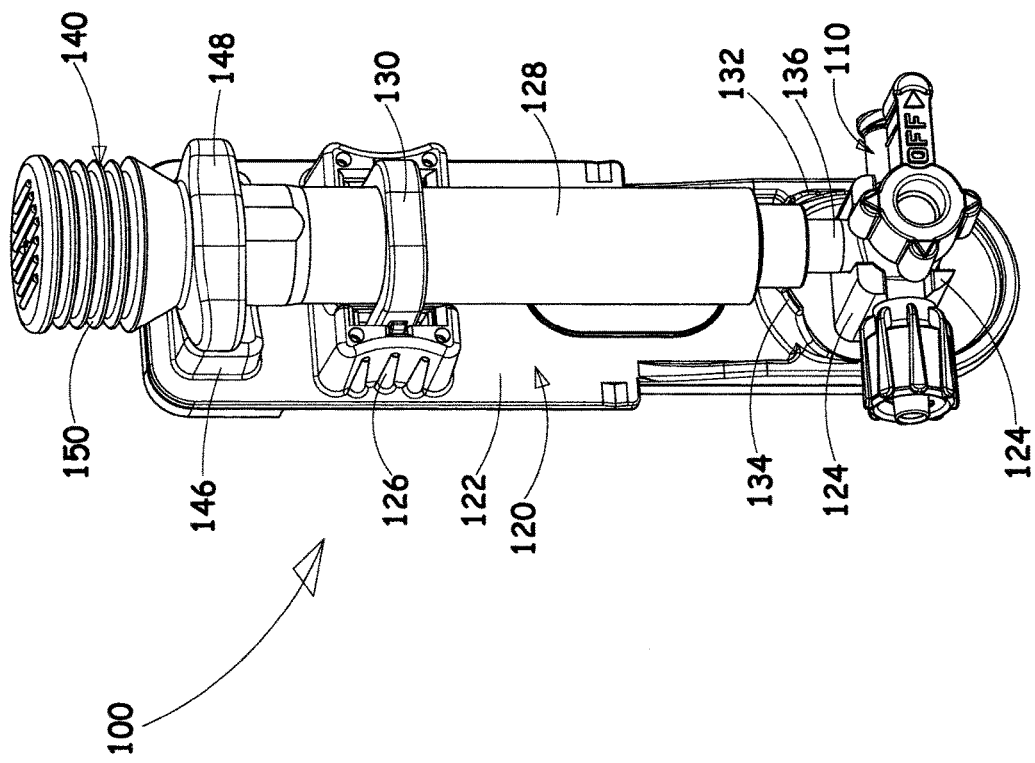
FIGS. 1A and 1B are respective simplified, assembled view and exploded view illustrations of a flushable fluid handling assembly constructed and operative in accordance with a preferred embodiment of the present invention.
Figure 1B:
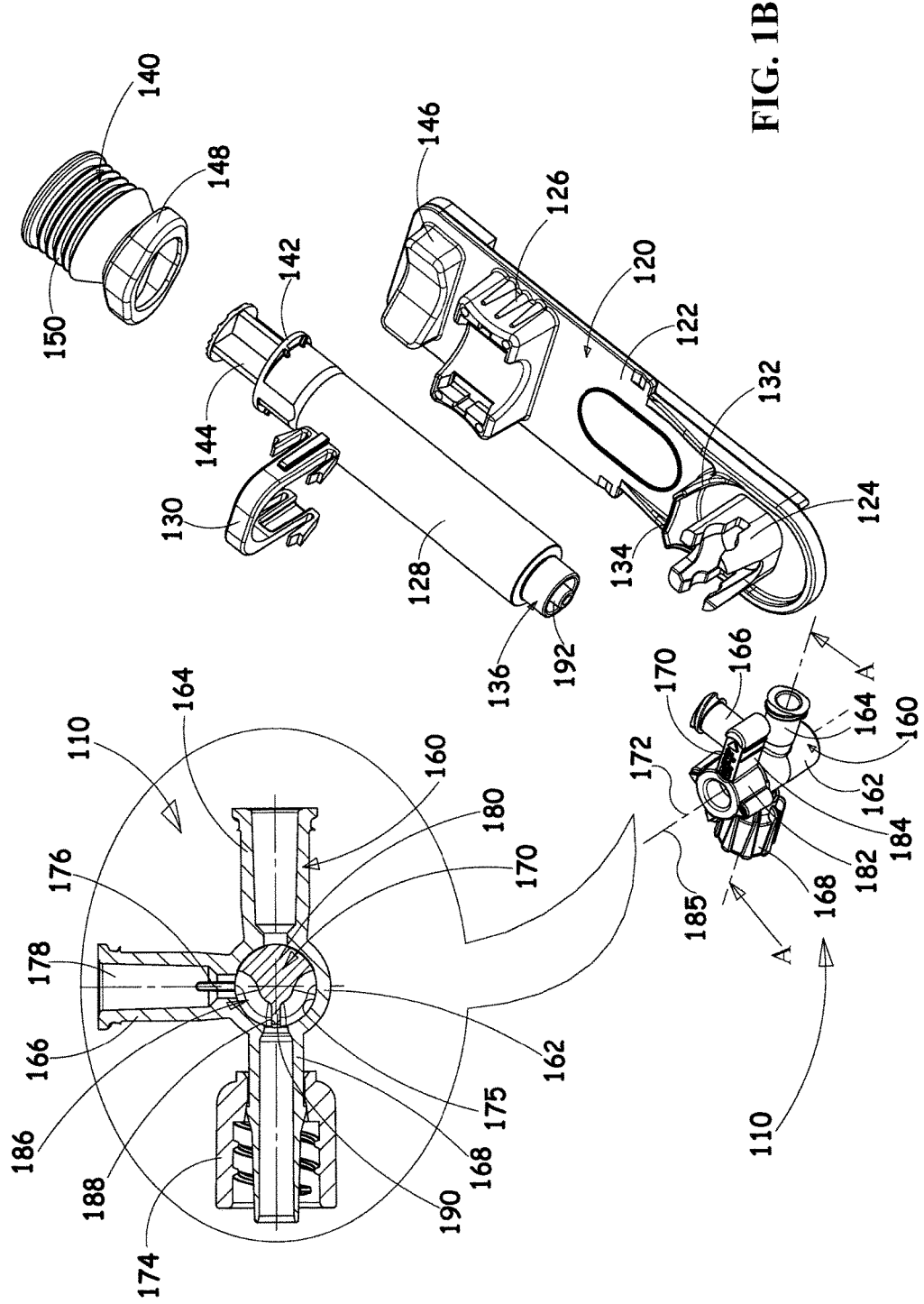

Reference is now made to FIGS. 1A and 1B, which are respective simplified, assembled view and exploded view illustrations of a flushable fluid handling assembly constructed and operative in accordance with a preferred embodiment of the present invention.

As seen in FIGS. 1A and 1B, there is provided a flushable fluid handling assembly 100 which includes a flushable stopcock assembly 110, preferably a MRVLS flushable stopcock assembly, which is commercially available from Elcam Medical Agricultural Cooperative Association Ltd., Kibbutz Baram, Israel and is described and claimed in at least one of U.S. Pat. Nos. 7,984,730; 8,534,321; 9,016,316 and pending U.S. patent application Ser. No. 14/665,850, which has been published as U.S. Patent Publication No. 2015/0196749, of the present assignee. Flushable stopcock assembly 110 is preferably snap-fit mounted onto a mounting base 120.

Mounting base 120 preferably includes a generally flat base portion 122 from which extend perpendicularly a pair of stopcock mounting arms 124, which retain flushable stopcock assembly 110 in snap-fit engagement. A syringe mounting portion 126 extends generally perpendicularly from flat base portion 122 for selectably receiving a conventional luer syringe 128. A snap-fit syringe retaining clip 130 engages syringe mounting portion 126 preferably in a snap-fit engagement for retaining syringe 128 in fixed engagement with mounting base 120.

A forward syringe mounting portion 132 extends generally perpendicularly from flat base portion 122 intermediate mounting arms 124 and mounting portion 126 and includes a curved cut out edge surface 134 which supports a forward portion 136 of syringe 128.

A resilient sealing cover 140 is sealingly mounted onto a flange 142 of syringe 128 over a piston 144 of syringe 128 and is supported by a cover support portion 146 of mounting base 120. Resilient sealing cover 140 preferably includes a mounting portion 148 and an extendible accordion-like portion 150.

Turning to flushable stopcock assembly 110, it is seen that the stopcock assembly 110 preferably includes a housing element 160 including a main tubular portion 162 and first, second and third ports, designated by reference numerals 164, 166 and 168, respectively. A handle element 170 is arranged to be seated within main tubular portion 162 of housing element 160. Main tubular portion 162 of housing element 160 is generally cylindrical, arranged about an axis 172, and ports 164, 166 and 168 extend in different directions therefrom, typically separated by 90 degrees about axis 172. Ports 164 and 166 are preferably female ports which preferably meet luer standard ISO 594-1, while port 168 is preferably a male port, which preferably meets luer standard ISO 594-1. A conventional nut 174 is preferably provided in association with port 168.

Preferably, port 166 is bifurcated by a fluid flow guide 176. Port 166 defines an internal volume 178. Handle element 170 preferably includes a shaft portion 180, which is integrally formed with a top portion 182 from which extends a finger-engageable protrusion 184. Shaft portion 180 is generally symmetrical about a shaft axis 185 and is preferably formed with a fluid flow passageway 186 which extends between selectable ones of ports 164, 166 and 168 depending on the rotational orientation of the handle element 170 relative to the housing element 160. Preferably extending radially and partially bifurcating the passageway 186 is a fluid flow guide 190, which directs the flow of liquid between ports 164 and 166 through passageway 186 into the internal volume 178 of port 166 for flushing thereof, when the handle element 170 is suitably positioned. A radially outward facing edge 188 of fluid flow guide 190 is formed such as not to completely prevent liquid flow therepast when fluid flow guide 190 is not located opposite a port.

It is a particular feature of the present invention that port 166 is fixedly and sealingly threadably connected to a luer connector 192 at the forward portion 136 of syringe 128 and cannot be disengaged therefrom without damaging either or both of the stopcock assembly 110 and the syringe 128.

Preferably, the flushable fluid handling assembly 100 is arranged with fluid flow guide 190 opposite either of ports 164 or 168 thereby providing fluid communication between internal volume 178 and the outside atmosphere, thereby to enable ETO sterilization of the internal volume 178 and that portion of the interior of the syringe that communicates therewith.

Reference is now made to FIGS. 2A, 2B, 2C, 2D, 2E, 2F, 2G, 2H, 2I, 2J and 2K, which are respective simplified illustrations of the flushable fluid handling assembly of FIGS. 1A & 1B arranged for blood sampling in accordance with one embodiment of the present invention in various operative orientations.

As seen in FIGS. 2A-2K, in a clinical setting, such as, for example, a blood donation center, the flushable fluid handling assembly 100 (FIGS. 1A and 1B) is typically connected as follows: Port 164 is connected via an IV (Intra Vascular) line 202 and a drip rate controller 204 to an elevated container, such as a bag 206, of sterile saline, preferably via a blood pressure measuring transducer 208, preferably a blood pressure measuring transducer which is commercially available from Elcam Medical Agricultural Cooperative Association Ltd., Kibbutz Baram, Israel and is described and claimed in U.S. Pat. No. 6,511,434. Port 168 is preferably connected to a conventional blood sampling port assembly 210 via an IV line 212. Blood sampling port 210 includes a housing 214 having three ports: a sampling port 216, fitted with a slitted septum 218 and a retaining cover 220, a port 226, which is coupled to IV line 212, and a port 236, which is coupled to an IV line 238, which is in turn connected to a circulatory system of a patient.

It is appreciated that the apparatus and the method described herein are not limited to medical therapeutic applications and uses and may be employed for other purposes.

Figure 2A:
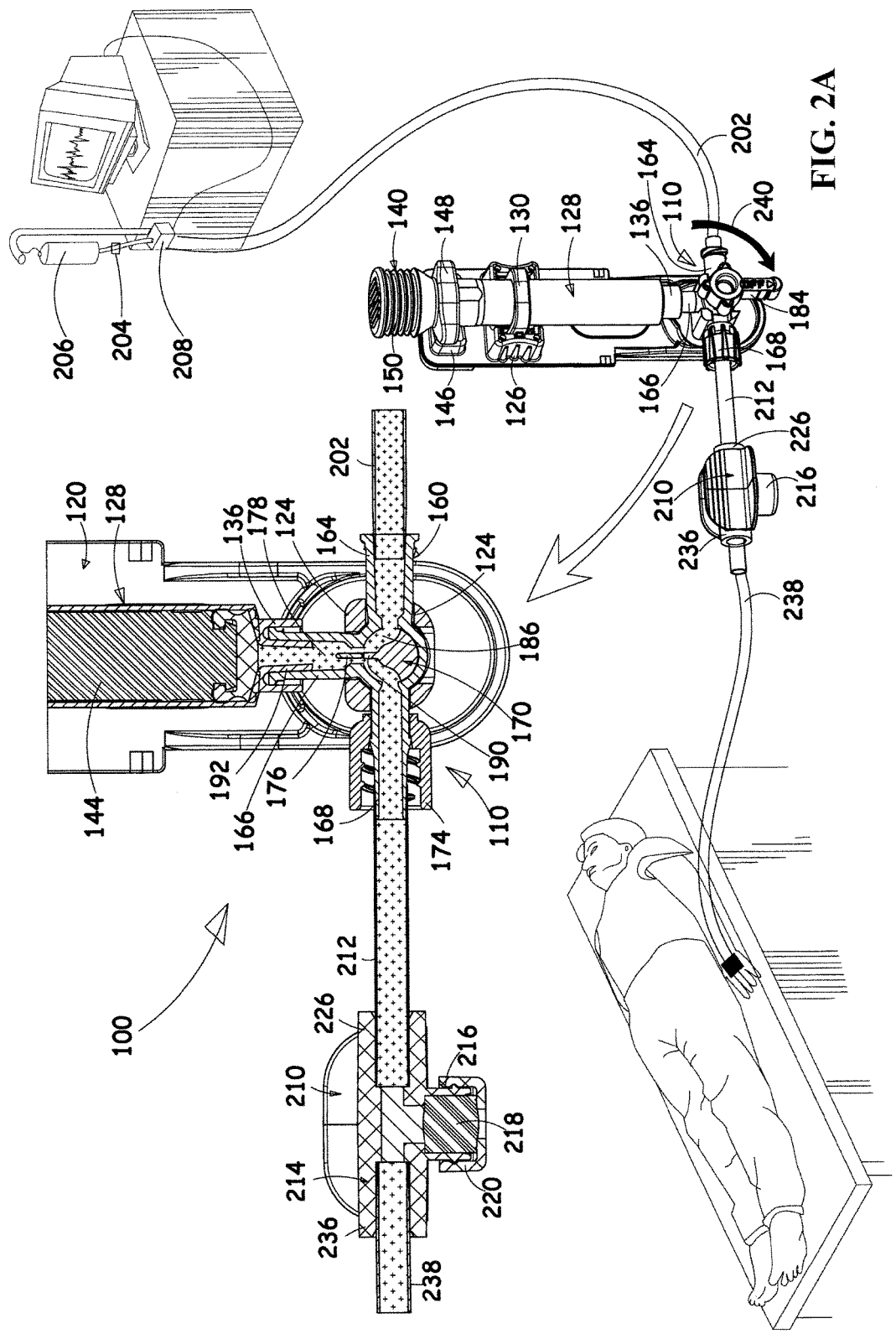
FIGS. 2A, 2B, 2C, 2D, 2E, 2F, 2G, 2H, 2I, 2J and 2K are respective simplified illustrations of the flushable fluid handling assembly of FIGS. 1A & 1B arranged for blood sampling in accordance with one embodiment of the present invention in various operative orientations.

Referring now specifically to FIG. 2A, it is seen that the flushable fluid handling assembly 100 is in a first operative orientation in which the handle element 170 of the flushable stopcock assembly 110 is positioned so as to provide fluid communication along passageway 186 between the first, second and third ports 164, 166 and 168 and the plunger 144 of the syringe 128 is in an extended position. IV lines 202, 212 and 238 as well as internal volume 178, an internal volume of the luer connector 192 and passageway 186 are all preferably filled with sterile saline. It is appreciated that handle element 170 has been rotated clockwise, in the sense of FIGS. 2A-2K, as indicated by an arrow 240, by 90 degrees from the sterilization orientation thereof shown in FIGS. 1A and 1B. The orientation shown in FIG. 2A is preferably a priming orientation whereby sterile saline from bag 206 fills the IV lines 202, 212 and 238 as well as internal volume 178, the internal volume of the luer connector 192 and passageway 186.

Figure 2B:
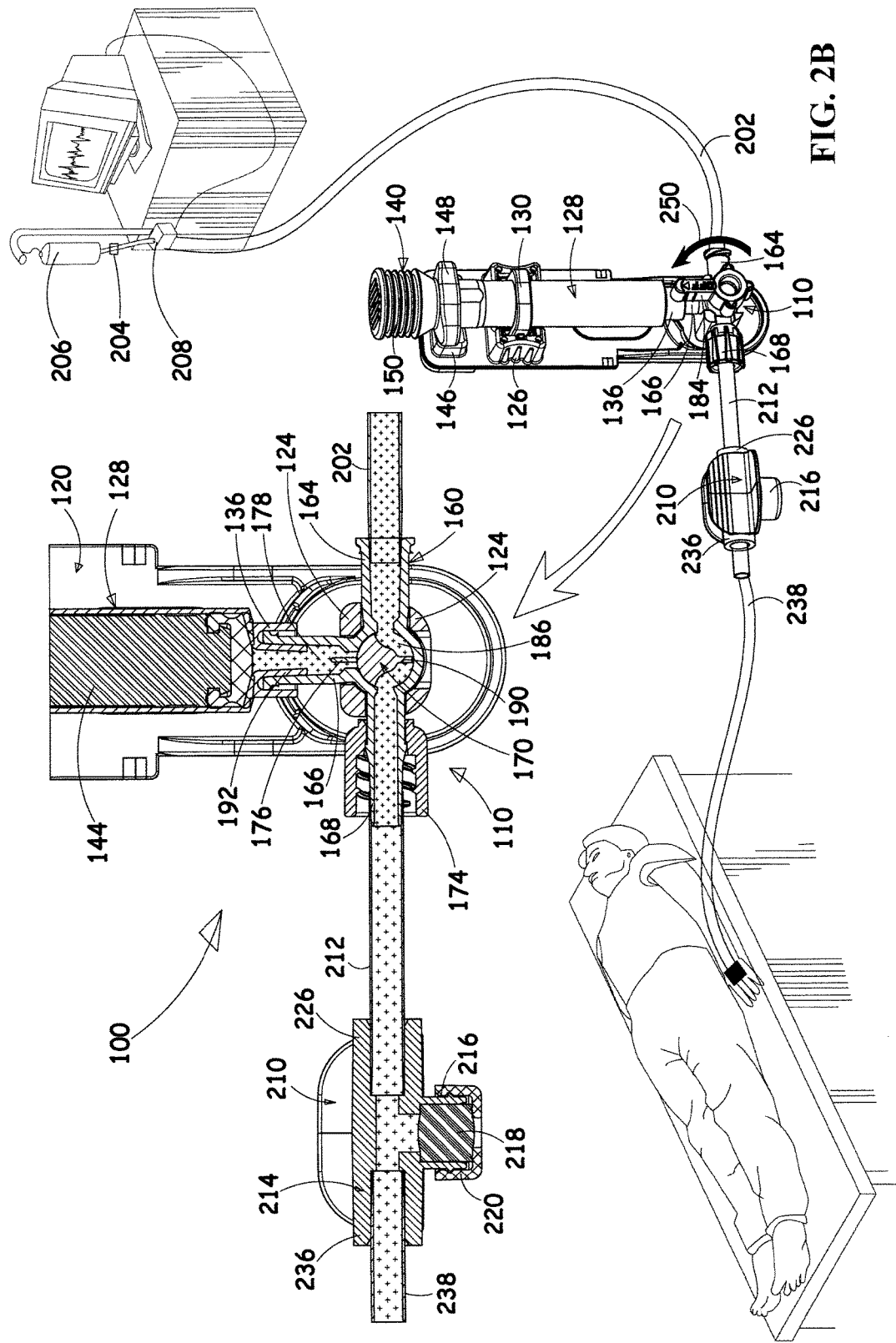

Referring now specifically to FIG. 2B, it is seen that the flushable fluid handling assembly 100 is in a second operative orientation in which the handle element 170 of the flushable stopcock assembly 110 is positioned so as to provide fluid communication along passageway 186 between only the first and third ports 164 and 168. The plunger 146 of the syringe 128 remains in an extended position. IV lines 202, 212 and 238 as well as internal volume 178, the internal volume of the luer connector 192 and passageway 186 preferably all remain filled with sterile saline. It is appreciated that handle element 170 has been rotated counterclockwise, in the sense of FIGS. 2A-2K, as indicated by an arrow 250, by 180 degrees from the orientation thereof shown in FIG. 2A. The orientation shown in FIG. 2B is particularly useful for blood pressure monitoring via transducer 208.

It is a particular feature of the embodiment illustrated in FIG. 2B that in the blood pressure monitoring operative orientation, handle element 170 of the flushable stopcock assembly 110 is positioned so as to isolate fluid communication along passageway 186 from the elastomeric piston of syringe 128 and thus avoid any damping thereby which could adversely affect a blood pressure measurement.

Figure 2C:
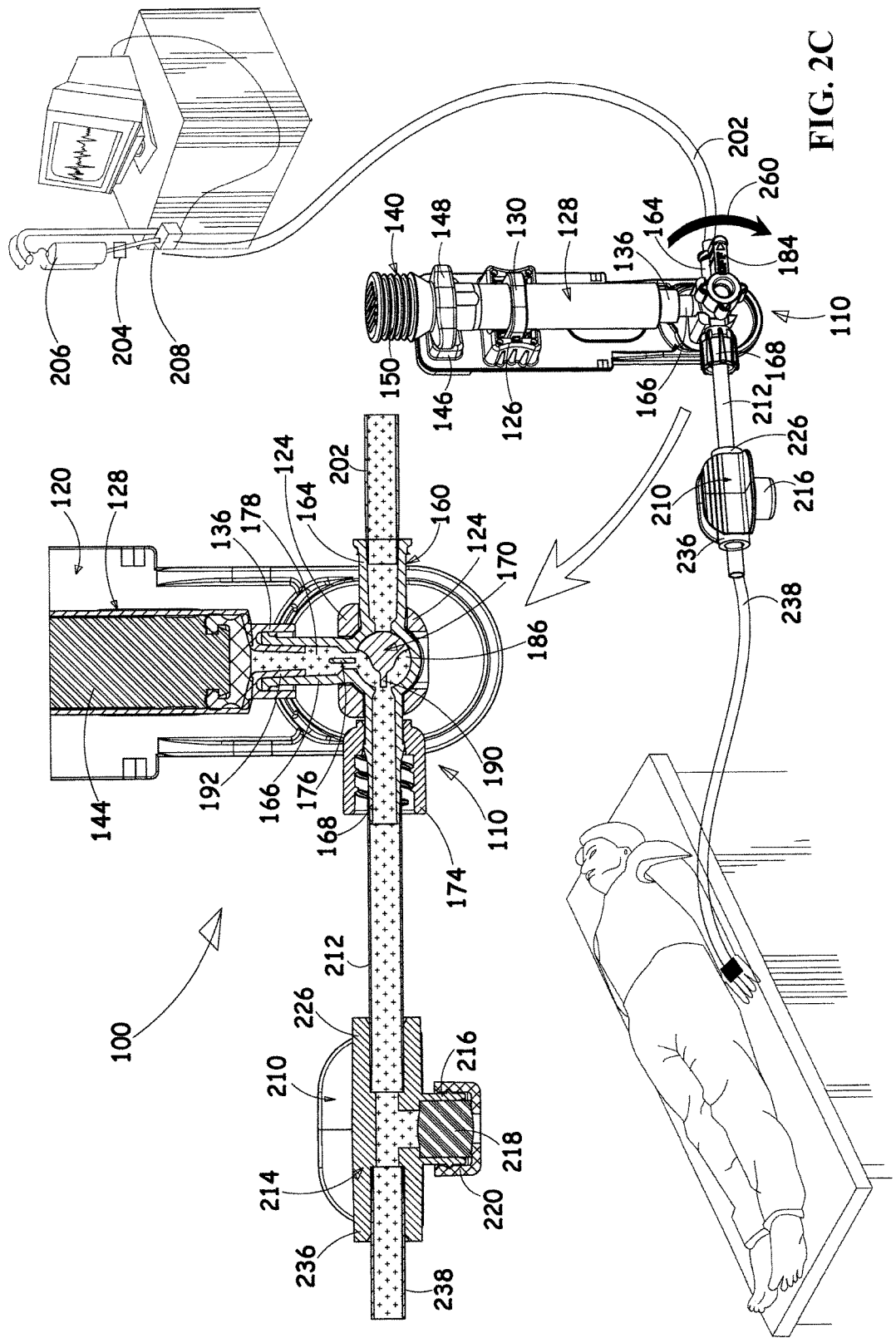

Referring now specifically to FIG. 2C, it is seen that the flushable fluid handling assembly 100 is in a third operative orientation in which the handle element 170 of the flushable stopcock assembly 110 is positioned so as to provide fluid communication along passageway 186 between only the second and third ports 166 and 168. The plunger 144 of the syringe 128 remains in an extended position. IV lines 202, 212 and 238 as well as internal volume 178, the internal volume of the luer connector 192 and passageway 186 preferably all remain filled with sterile saline. It is appreciated that handle element 170 has been rotated clockwise, in the sense of FIGS. 2A-2K, as indicated by an arrow 260, by 90 degrees from the orientation thereof shown in FIG. 2B. The orientation shown in FIG. 2C is particularly useful just prior to drawing blood.

Figure 2D:
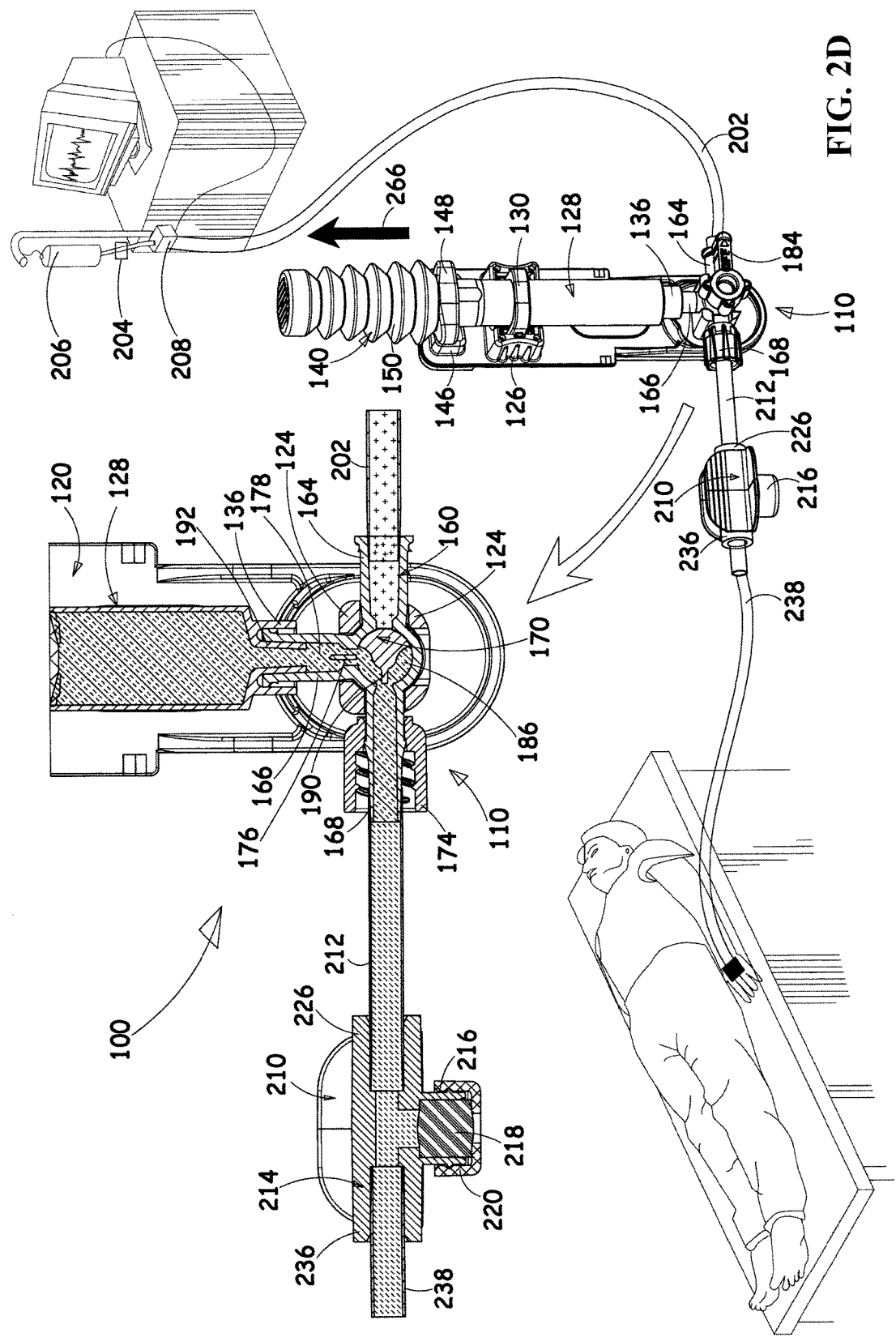

Referring now specifically to FIG. 2D, it is seen that the flushable fluid handling assembly 100 is in a fourth operative orientation in which the handle element 170 of the flushable stopcock assembly 110 is positioned so as to provide fluid communication along passageway 186 between only the second and third ports 166 and 168. The plunger 144 of the syringe 128 is now displaced, as indicated by an arrow 266, into a retracted position, thereby drawing blood from the patient into IV lines 212 and 238, as well as diluted blood into internal volume 178, the internal volume of the luer connector 192 and passageway 186. It is appreciated that handle element 170 has not been rotated from the orientation thereof shown in FIG. 2C. The orientation shown in FIG. 2D is particularly useful for drawing blood.

Figure 2E:
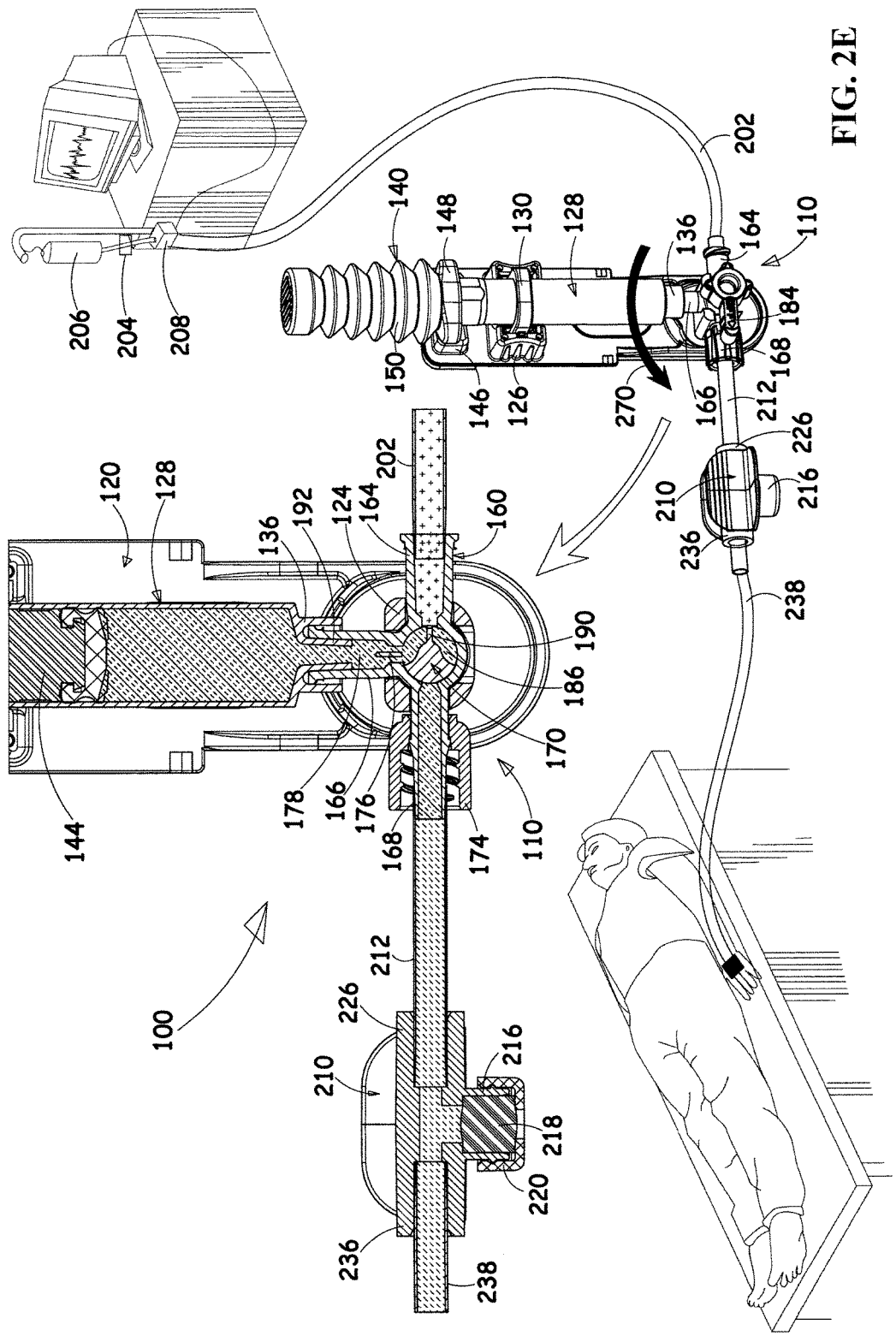

Referring now specifically to FIG. 2E, it is seen that the flushable fluid handling assembly 100 is in a fifth operative orientation in which the handle element 170 of the flushable stopcock assembly 110 is positioned so as to provide fluid communication along passageway 186 between only the first and second ports 164 and 166. The plunger 144 of the syringe 128 remains in a retracted position. Blood in IV lines 212 and 238 is isolated from passageway 186 and from internal volume 178 and the internal volume of the luer connector 192. It is appreciated that handle element 170 has been rotated counterclockwise, in the sense of FIGS. 2A-2K, as indicated by an arrow 270, by 180 degrees from the orientation thereof shown in FIG. 2D. The orientation shown in FIG. 2E is particularly useful just before sampling blood.

Figure 2F:
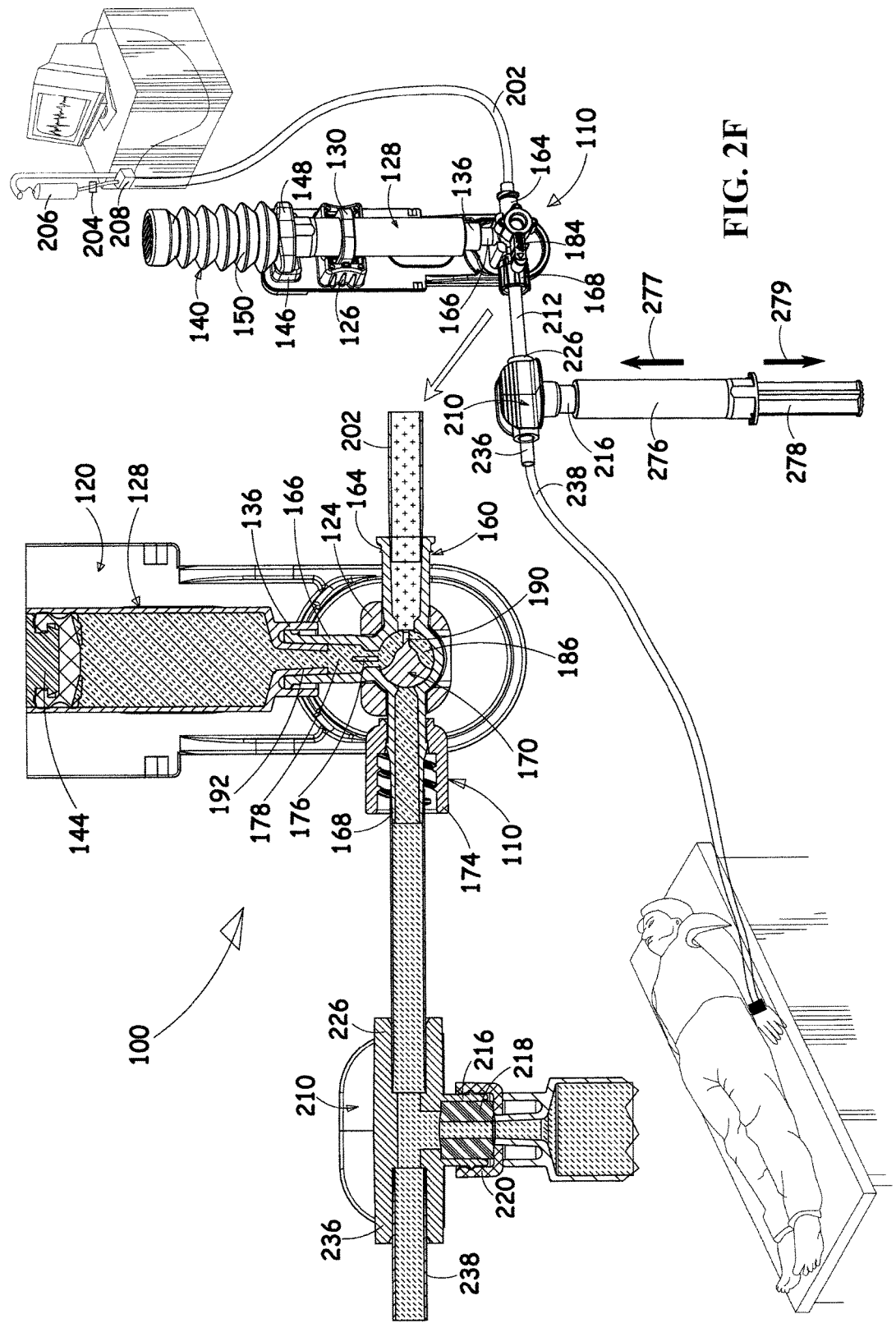

Referring now specifically to FIG. 2F, it is seen that the flushable fluid handling assembly 100 remains in the fifth operative orientation in which the handle element 170 of the flushable stopcock assembly 110 is positioned so as to provide fluid communication along passageway 186 between only the first and second ports 164 and 166. The plunger 144 of the syringe 128 remains in a retracted position. Blood in IV lines 212 and 238 is isolated from passageway 186 and from internal volume 178 and the internal volume of the luer connector 192. It is appreciated that handle element 170 has not been rotated from the orientation thereof shown in FIG. 2E. What has changed is that a blood sampling syringe 276 has been inserted at the slitted septum 218 of the blood sampling port assembly 210, as indicated by an arrow 277, and its piston 278 has been retracted, as indicated by an arrow 279, thereby drawing blood from the patient via IV line 238 into the interior of syringe 276. The orientation shown in FIG. 2F is particularly useful for sampling blood.

Figure 2G:
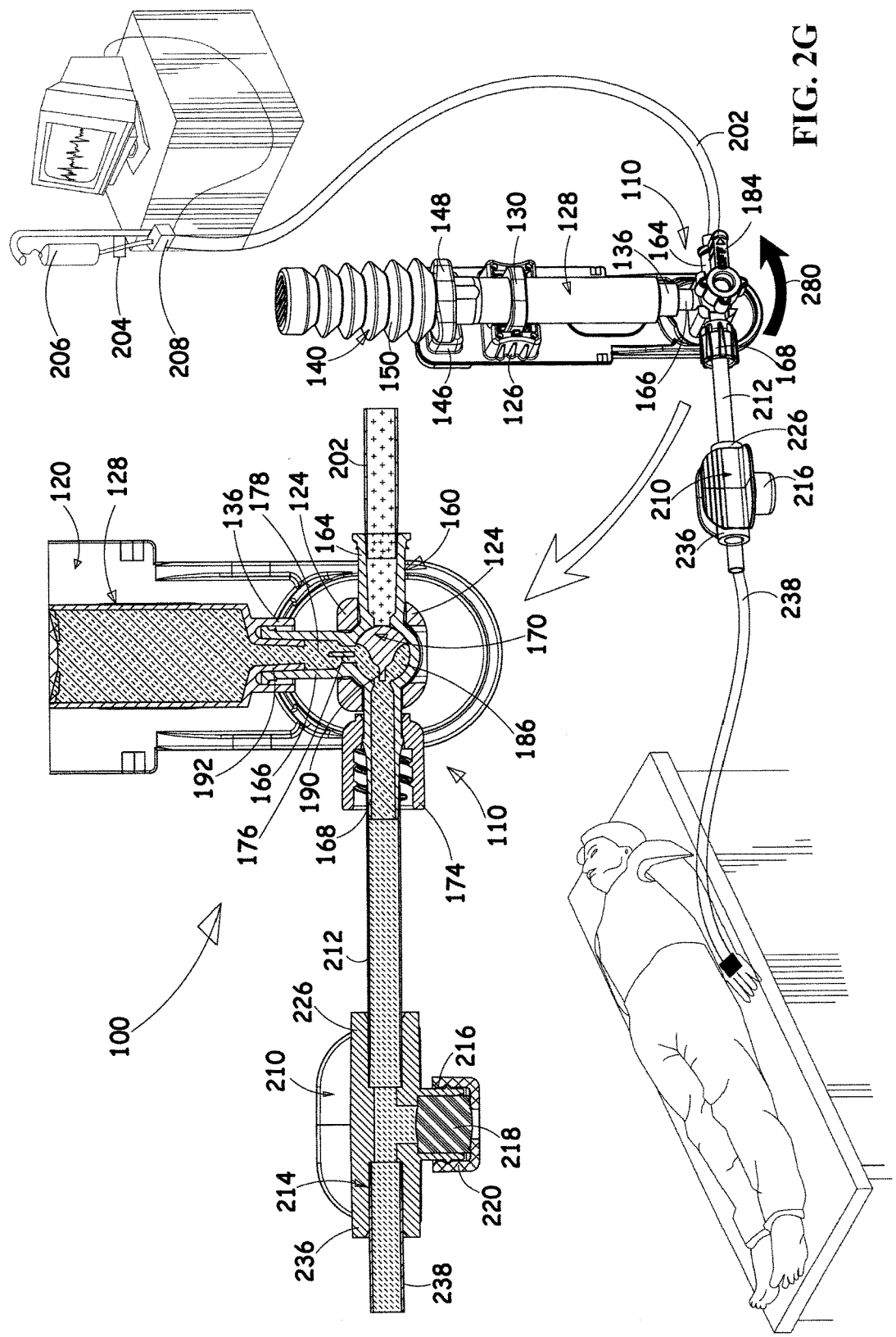

Referring now specifically to FIG. 2G, it is seen that the syringe 276 has been disengaged from the slitted septum 218 and that flushable fluid handling assembly 100 is now in a sixth operative orientation in which the handle element 170 of the flushable stopcock assembly 110 is positioned so as to provide fluid communication along passageway 186 between only the second and third ports 166 and 168. The plunger 144 of the syringe 128 remains in a retracted position. Blood in IV lines 212 and 238 is no longer isolated from passageway 186, from internal volume 178 and the internal volume of the luer connector 192. It is appreciated that handle element 170 has been rotated counterclockwise, in the sense of FIGS. 2A-2K, as indicated by an arrow 280, by 180 degrees from the orientation thereof shown in FIG. 2F. The orientation shown in FIG. 2G is particularly useful just before directing blood back to the patient from passageway 186, from internal volume 178 and the internal volume of the luer connector 192 and the remainder of the interior of the syringe 128.

Figure 2H:
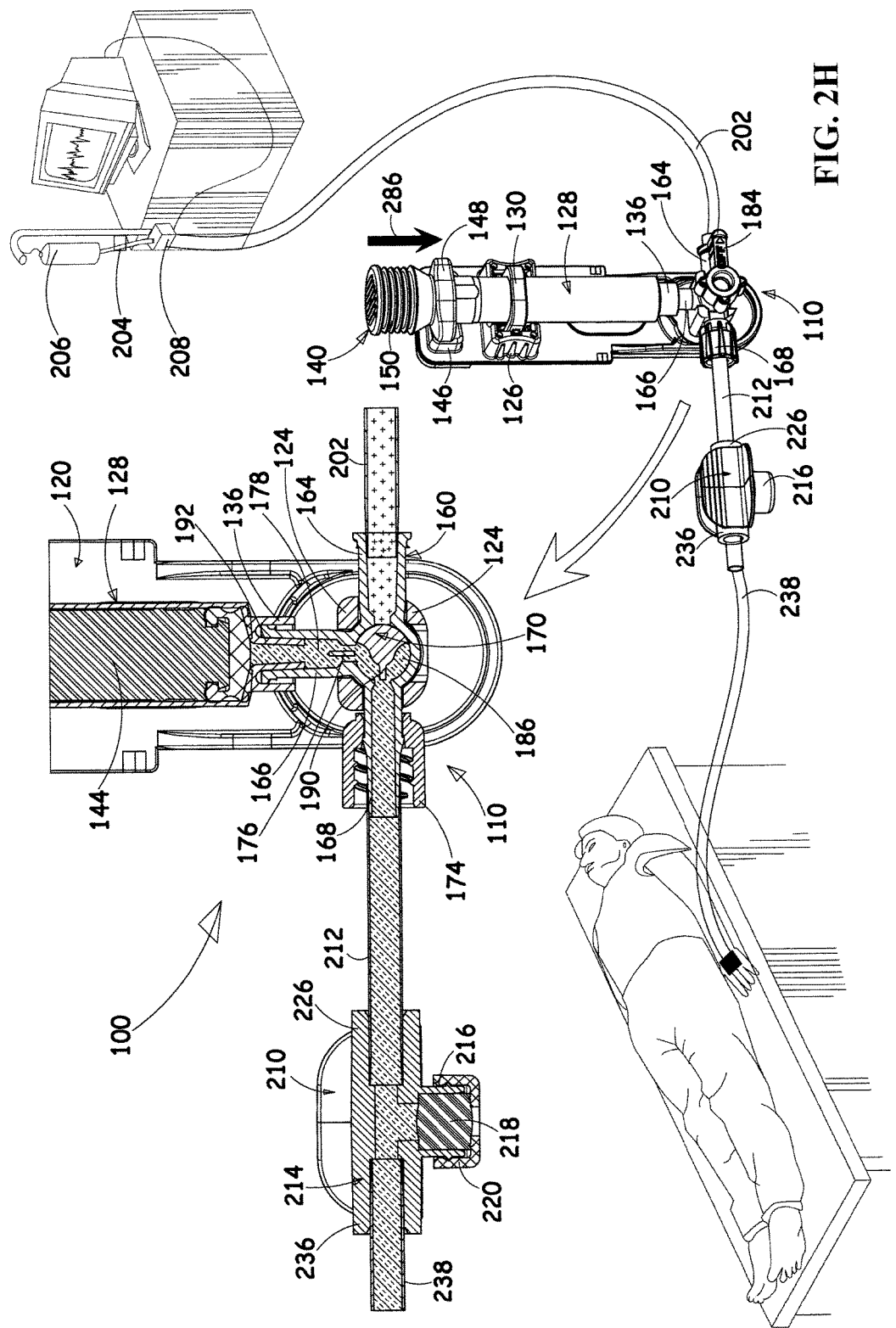

Referring now specifically to FIG. 2H, it is seen that the flushable fluid handling assembly 100 is now in a seventh operative orientation in which the handle element 170 of the flushable stopcock assembly 110 remains positioned so as to provide fluid communication along passageway 186 between only the second and third ports 166 and 168. The plunger 144 of the syringe 128 is displaced, as indicated by an arrow 286, to an extended position, thereby forcing diluted blood from the interior of the syringe 128, the internal volume of the luer connector 192, internal volume 178 and the passageway 186 out through the third port 168. It is appreciated that handle element 170 has not been rotated from the orientation thereof shown in FIG. 2G. The orientation shown in FIG. 2H is particularly useful for directing blood back to the patient from passageway 186, from internal volume 178 and the internal volume of the luer connector 192 and the remainder of the interior of the syringe 128.

Figure 2I:
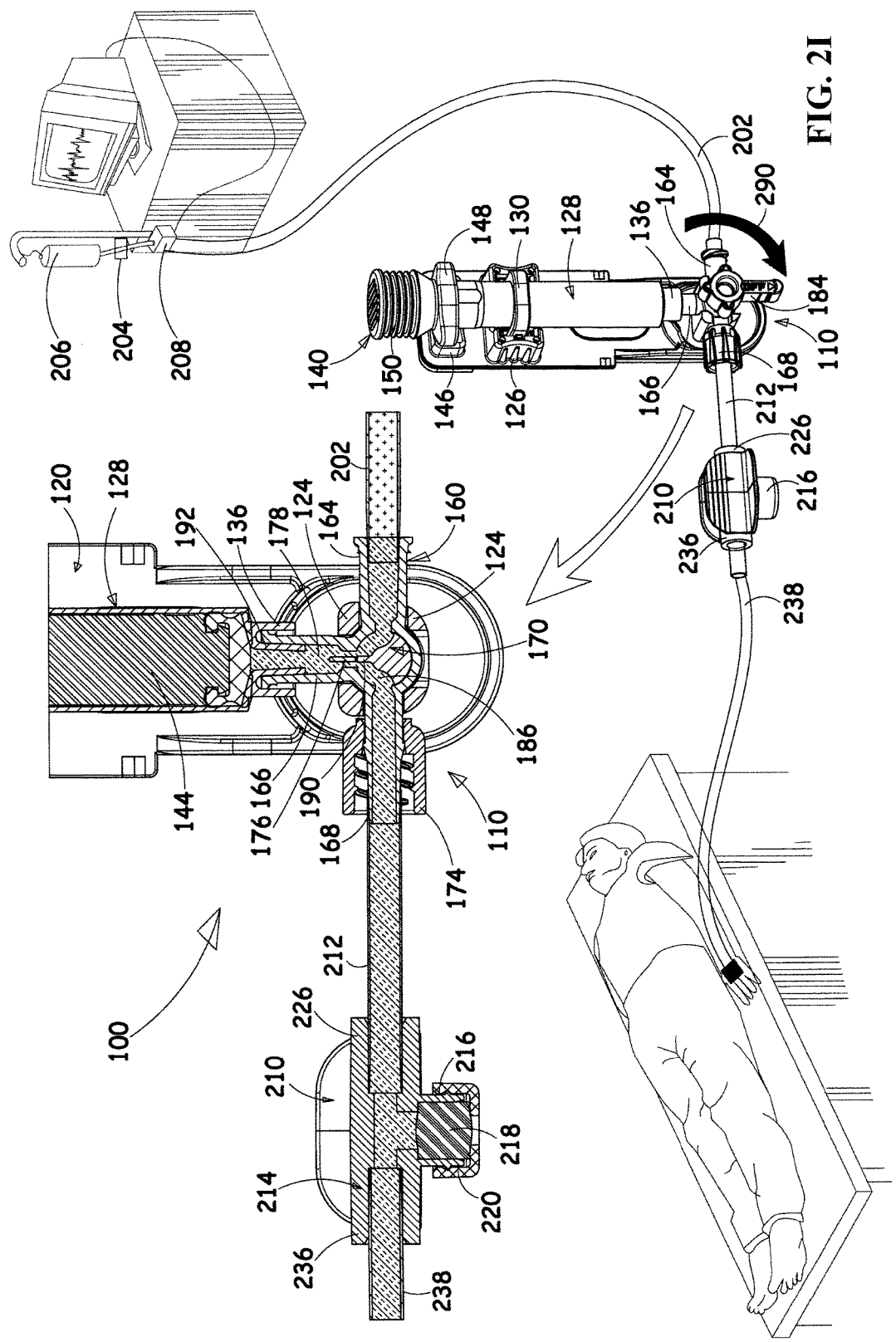

Referring now specifically to FIG. 2I, it is seen that the flushable fluid handling assembly 100 is now in an eighth operative orientation in which the handle element 170 of the flushable stopcock assembly 110 is positioned so as to provide fluid communication along passageway 186 between the first, second and third ports 164, 166 and 168. The plunger 144 of the syringe 128 remains in an extended position. It is appreciated that handle element 170 has been rotated clockwise, in the sense of FIGS. 2A-2K, as indicated by an arrow 290, by 90 degrees from the orientation thereof shown in FIG. 2H. The orientation shown in FIG. 2I is particularly useful just before flushing of internal volume 178, the internal volume of the luer connector 192 and passageway 186.

Figure 2J:
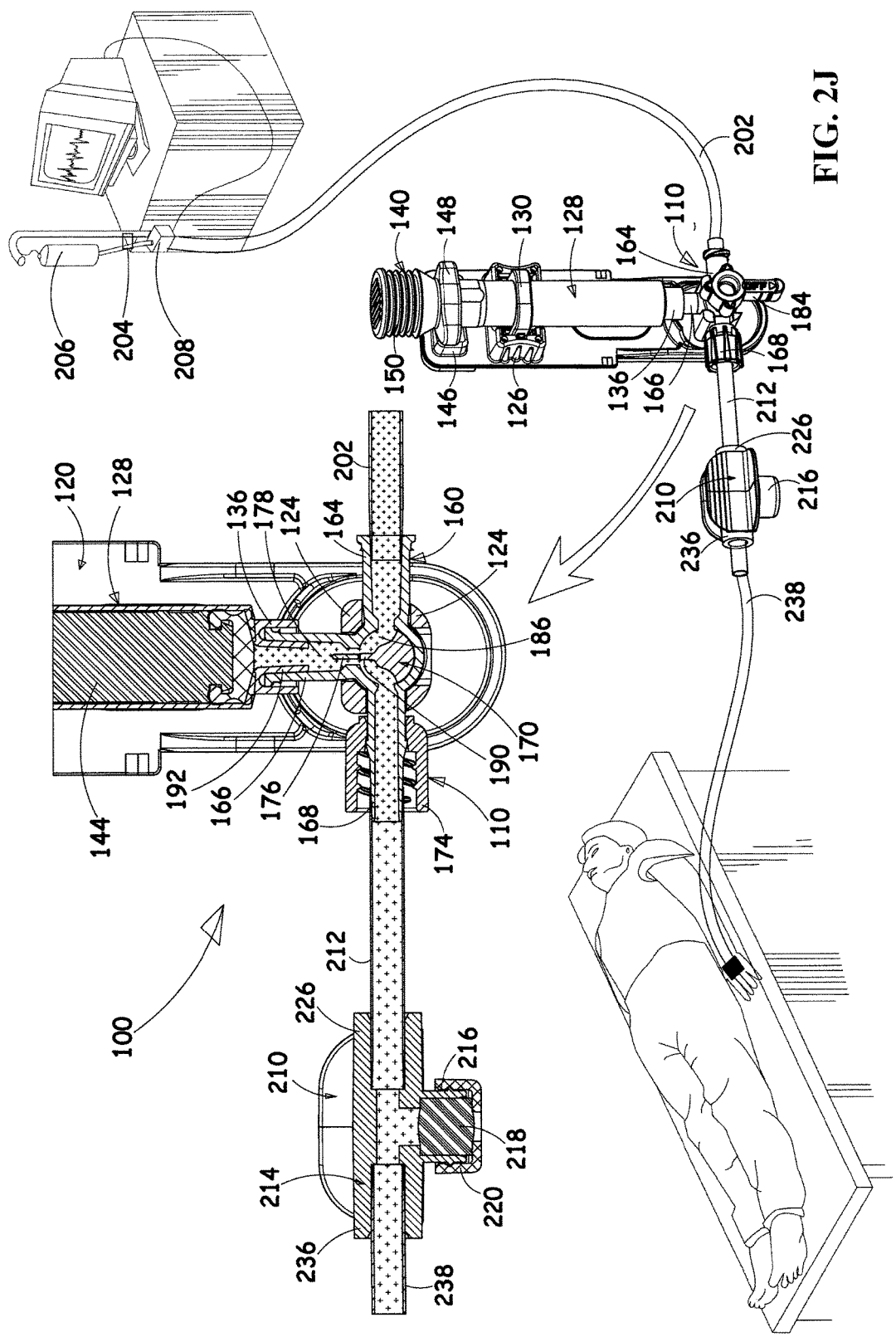

Referring now specifically to FIG. 2J, it is seen that the flushable fluid handling assembly 100 is now in a ninth operative orientation in which the handle element 170 of the flushable stopcock assembly 110 remains positioned so as to provide fluid communication along passageway 186 between the first, second and third ports 164, 166 and 168. The plunger 144 of the syringe 128 remains in an extended position. It is appreciated that handle element 170 has not been rotated from the orientation thereof shown in FIG. 2I.

It is a particular feature of an embodiment of the present invention that sterile saline from bag 206 has flowed under gravity in response to operation of transducer 208 in a flushing mode and has flushed internal volume 178, the internal volume of the luer connector 192 and passageway 186 as sterile saline flowed past both fluid flow guide 176 and fluid flow guide 190, which are arranged along a single longitudinal axis in this operative orientation. It is appreciated that in this operative orientation, a fluid flow of first fluid arriving from bag 206 via IV line 202 and first port 164 flows through fluid flow passageway 186 and does not flow entirely through said second port 166 whose internal volume is being flushed. This fluid flow of first fluid around fluid flow guides 176 and 190 enables flushing of any diluted blood that has remained in at least one of the internal volume of the luer connector 192, internal volume 178 and passageway 186.

Figure 2K:
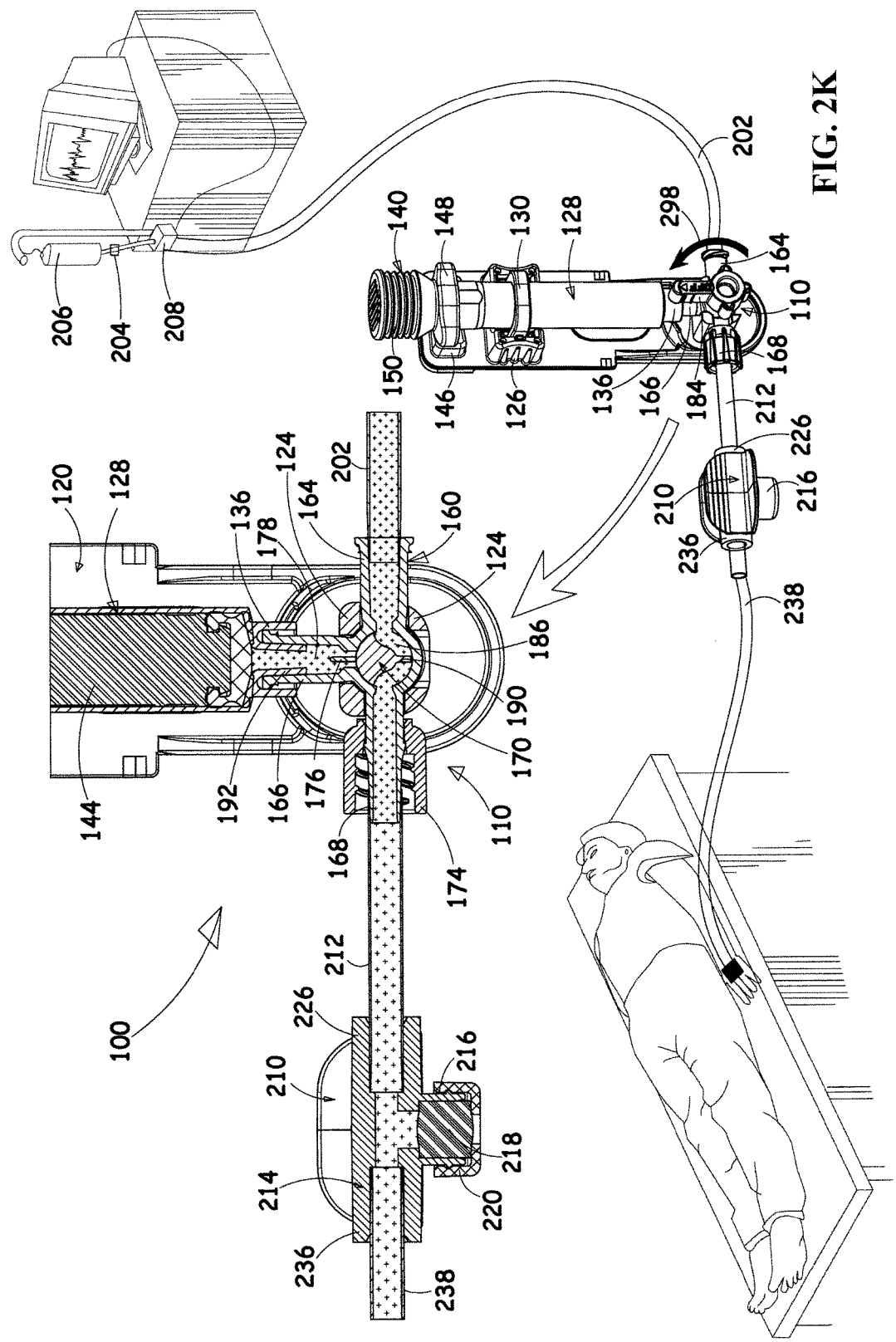

Referring now specifically to FIG. 2K, it is seen that the flushable fluid handling assembly 100 is now in a tenth operative orientation in which the handle element 170 of the flushable stopcock assembly 110 is positioned so as to provide fluid communication along passageway 186 between only the first and third ports 164 and 168. The plunger 144 of the syringe 128 remains in an extended position. It is appreciated that handle element 170 has been rotated counterclockwise, in the sense of FIGS. 2A-2K, as indicated by an arrow 298, by 180 degrees from the orientation thereof shown in FIG. 2J. The flushable fluid handling assembly 100 is in an operative orientation suitable for blood pressure monitoring by transducer 208.

Reference is now made to FIGS. 3A, 3B, 3C, 3D, 3E, 3F, 3G, 3H, 3I, 3J and 3K, which are respective simplified illustrations of the flushable fluid handling assembly of FIGS. 1A & 1B arranged for blood sampling in accordance with another embodiment of the present invention in various operative orientations.

As seen in FIGS. 3A-3K, in a clinical setting, such as, for example, a blood donation center, the flushable fluid handling assembly 100 (FIGS. 1A and 1B) is typically connected as follows: Port 164 is connected via an IV line 302 and a drip rate controller 304 to an elevated container, such as a bag 306, of sterile saline, preferably via a blood pressure measuring transducer 308, preferably a blood pressure measuring transducer which is commercially available from Elcam Medical Agricultural Cooperative Association Ltd., Kibbutz Baram, Israel and is described and claimed in U.S. Pat. No. 6,511,434. Port 168 is preferably connected to a commercially available blood sampling port assembly 310, preferably a MRVLS flushable stopcock assembly, which is commercially available from Elcam Medical Agricultural Cooperative Association Ltd., Kibbutz Baram, Israel and is described and claimed in at least one of U.S. Pat. Nos. 7,984,730; 8,534,321; 9,016,316 and pending U.S. patent application Ser. No. 14/665,850 of the present assignee, via an IV line 312.

Blood sampling port assembly 310 preferably includes a housing portion 314, a main tubular portion 316 and first, second and third ports, designated by reference numerals 318, 320 and 322, respectively. A handle element 324 is arranged to be seated within main tubular portion 316 of housing element 314. Main tubular portion 316 of housing portion 314 is generally cylindrical, arranged about an axis 326, and ports 318, 320 and 322 extend in different directions therefrom, typically separated by 90 degrees about axis 326. Port 322 is preferably a female port, which preferably meets luer standard ISO 594-1, while port 318 is preferably a male port, which preferably meets luer standard ISO 594-1. A conventional nut 328 is preferably provided in association with port 318.

Port 320 is preferably equipped with a valve 330 employing an elastomeric element 332, held in place by a cap 334, which is welded or otherwise fixed to housing element 314. Elastomeric element 332 and cap 334 are commercially available from Halkey-Roberts Corporation of St. Petersburg, Fla., USA and described in one or more of U.S. Pat. Nos. 6,651,956; 6,089,541 and 6,036,171, the disclosures of which are hereby incorporated by reference. Alternatively, valves and valve elements commercially available from other sources, such as Becton-Dickinson, Cardinal, Medegen and Filtertek, may be employed.

Port 322 is coupled to an IV line 338, which is in turn connected to a circulatory system of a patient.

Preferably, port 320 is bifurcated by a fluid flow guide 340. Port 320 defines an internal volume 342. Handle element 324 preferably includes a shaft portion 344, which is integrally formed with a top portion 346 from which extends a finger-engageable protrusion 348. Shaft portion 344 is generally symmetrical about a shaft axis 350 and is preferably formed with a fluid flow passageway 352 which extends between selectable ones of ports 318, 320 and 322 depending on the rotational orientation of the handle element 324 relative to the housing element 314. Preferably extending radially and partially bifurcating the passageway 352 is a fluid flow guide 354, which directs the flow of liquid between ports 318, 320 and 322 through passageway 352 into the internal volume 342 of port 320 for flushing thereof, when the handle element 324 is suitably positioned. A radially outward facing edge 356 of fluid flow guide 354 is formed such as not to completely prevent liquid flow therepast when fluid flow guide 354 is not located opposite a port.

It is appreciated that the apparatus and the method described herein are not limited to medical therapeutic applications and uses and may be employed for other purposes.

Figure 3A:
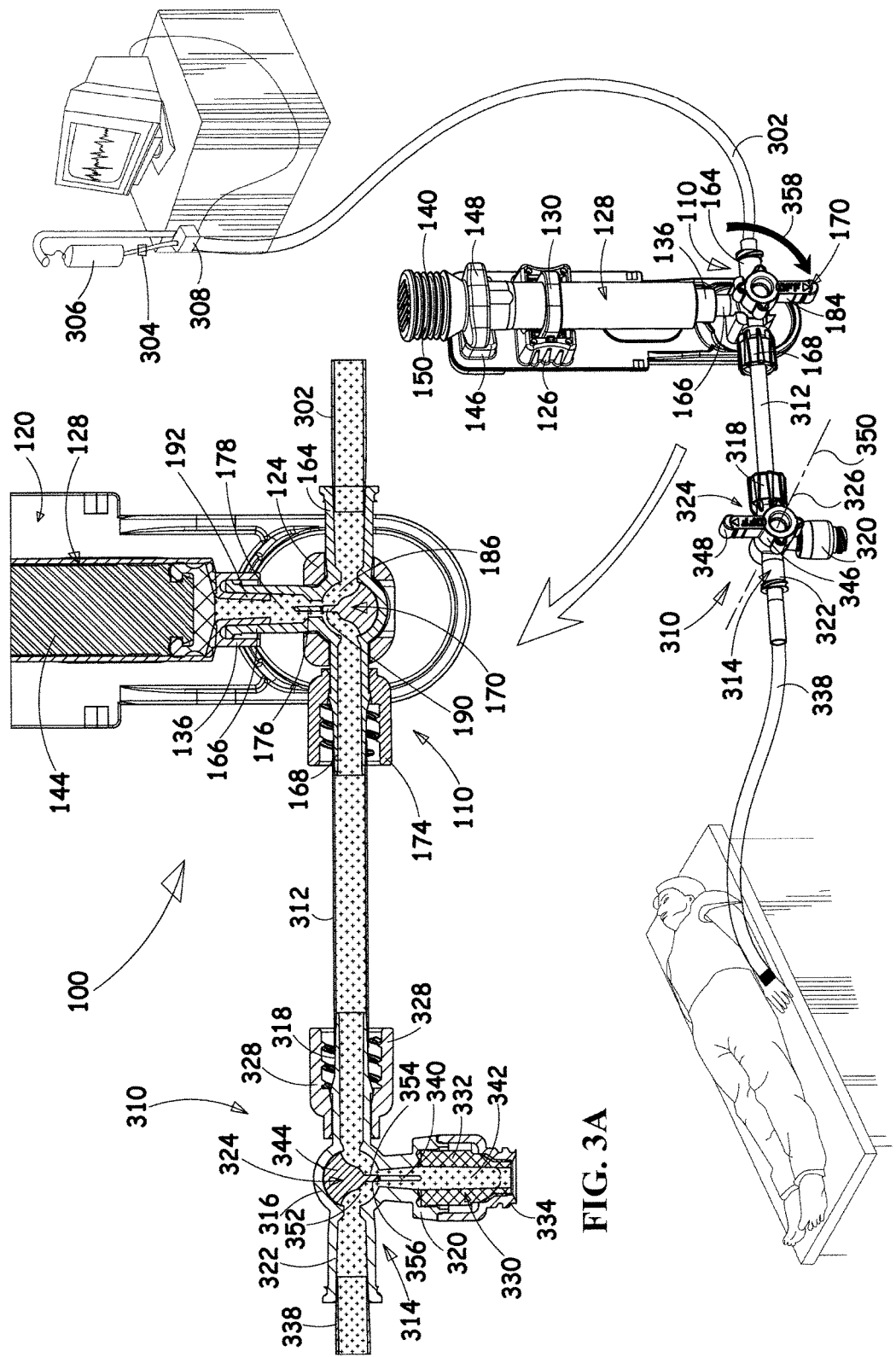
FIGS. 3A, 3B, 3C, 3D, 3E, 3F, 3G, 3H, 3I, 3J and 3K are respective simplified illustrations of the flushable fluid handling assembly of FIGS. 1A & 1B arranged for blood sampling in accordance with another embodiment of the present invention in various operative orientations.

Referring now specifically to FIG. 3A, it is seen that the flushable fluid handling assembly 100 is in a first operative orientation in which the handle element 170 of the flushable stopcock assembly 110 is positioned so as to provide fluid communication along passageway 186 between the first, second and third ports 164, 166 and 168 and the plunger 144 of the syringe 128 is in an extended position. IV lines 302, 312 and 338 as well as internal volume 178, the internal volume of the luer connector 192 and passageway 186 are all preferably filled with sterile saline. It is appreciated that handle element 170 has been rotated clockwise, in the sense of FIGS. 3A-3K, as indicated by an arrow 358, by 90 degrees from the sterilization orientation thereof shown in FIGS. 1A and 1B. Here handle element 324 of the blood sampling port assembly 310 is positioned so as to provide fluid communication along passageway 352 between the first, second and third ports 318, 320 and 322. The orientation shown in FIG. 3A is preferably a priming orientation whereby sterile saline from bag 306 fills the IV lines 302, 312 and 338 as well as internal volume 178, the internal volume of the luer connector 192 and passageway 186.

Figure 3B:
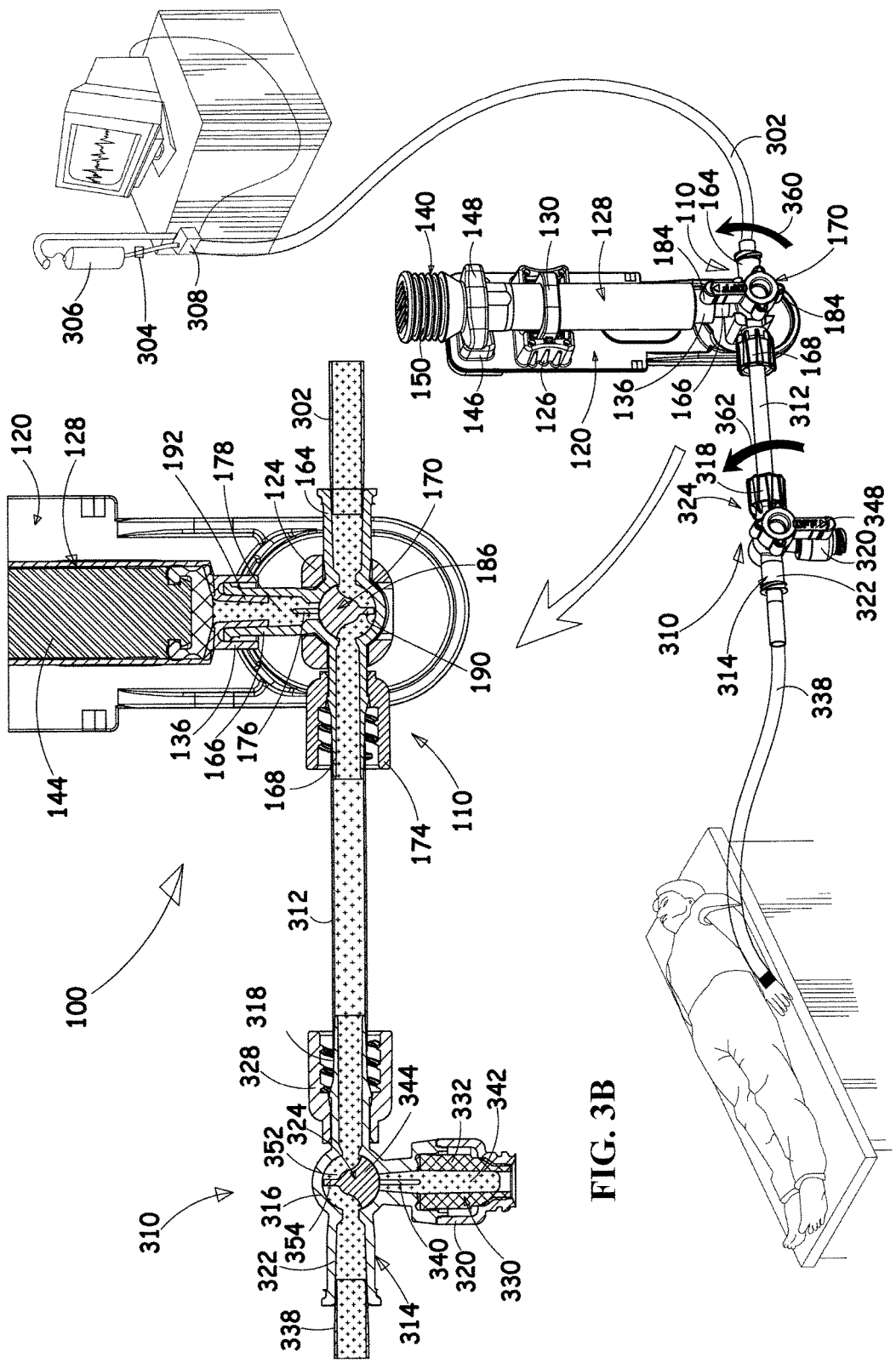

Referring now specifically to FIG. 3B, it is seen that the flushable fluid handling assembly 100 is in a second operative orientation in which the handle element 170 of the flushable stopcock assembly 110 is positioned so as to provide fluid communication along passageway 186 between only the first and third ports 164 and 168. The plunger 144 of the syringe 128 remains in an extended position. IV lines 302, 312 and 338 as well as internal volume 178, the internal volume of the luer connector 192 and passageway 186 preferably all remain filled with sterile saline. It is appreciated that handle element 170 has been rotated counterclockwise, in the sense of FIGS. 3A-3K, as indicated by an arrow 360, by 180 degrees from the orientation thereof shown in FIG. 3A. The orientation shown in FIG. 3B is particularly useful for blood pressure monitoring via transducer 308.

It is a particular feature of the embodiment illustrated in FIG. 3B that in the blood pressure monitoring operative orientation, handle element 170 of the flushable stopcock assembly 110 is positioned so as to isolate fluid communication along passageway 186 from the elastomeric piston of syringe 128 and thus avoid any damping thereby which could adversely affect a blood pressure measurement.

It is a particular feature of the embodiment illustrated in FIG. 3B that in the blood pressure monitoring operative orientation, handle element 324 of the blood sampling port assembly 310 is positioned so as to isolate fluid communication along passageway 352 from elastomeric element 330 and thus avoid any damping thereby which could adversely affect a blood pressure measurement. It is seen that handle element 324 has been rotated counterclockwise, in the sense of FIGS. 3A-3K, as indicated by an arrow 362, by 180 degrees from the orientation thereof shown in FIG. 3A.

Figure 3C:
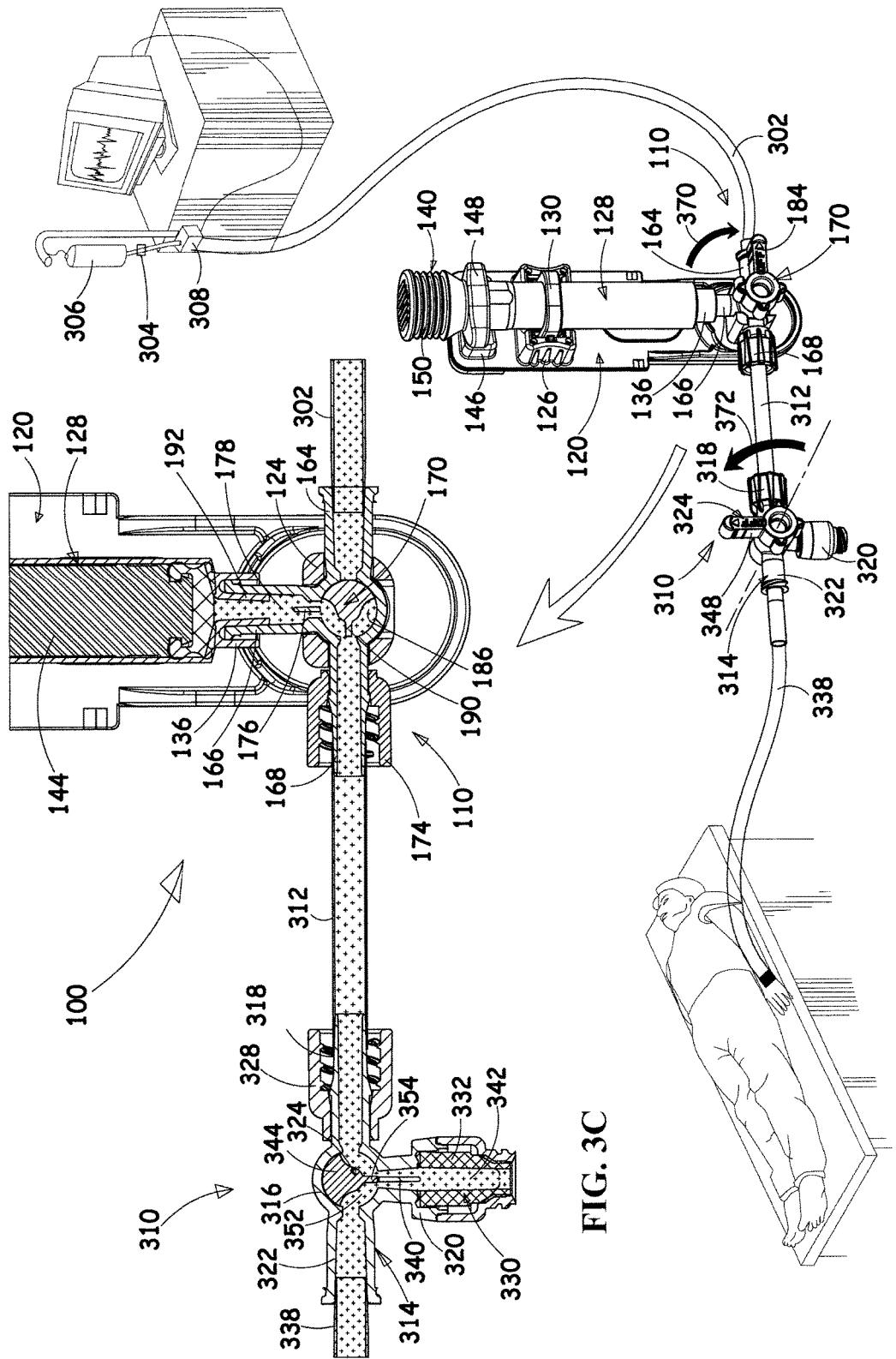

Referring now specifically to FIG. 3C, it is seen that the flushable fluid handling assembly 100 is in a third operative orientation in which the handle element 170 of the flushable stopcock assembly 110 is positioned so as to provide fluid communication along passageway 186 between only the second and third ports 166 and 168. The plunger 144 of the syringe 128 remains in an extended position. IV lines 302, 312 and 338 as well as internal volume 178, the internal volume of the luer connector 192 and passageway 186 preferably all remain filled with sterile saline. It is appreciated that handle element 170 has been rotated clockwise, in the sense of FIGS. 3A-3K, as indicated by an arrow 370, by 90 degrees from the orientation thereof shown in FIG. 3B. The orientation shown in FIG. 3C is particularly useful just prior to drawing blood.

It is seen that handle element 324 of the blood sampling port assembly 310 is positioned so as to provide fluid communication along passageway 352 between all of first, second and third ports 318, 320 and 322. It is seen that handle element 324 has been rotated counterclockwise, in the sense of FIGS. 3A-3K, as indicated by an arrow 372, by 180 degrees from the orientation thereof shown in FIG. 3B.

Figure 3D:
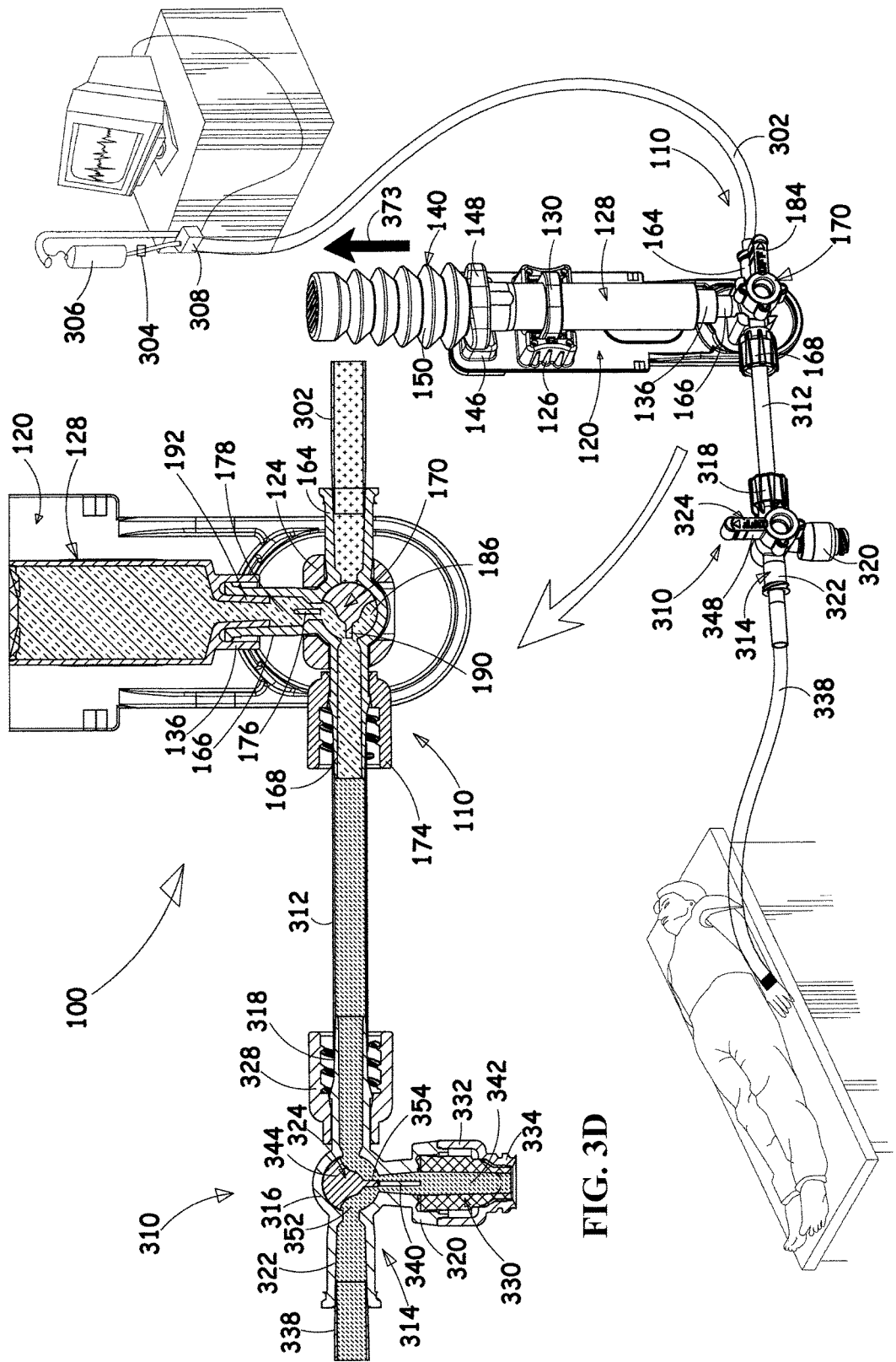

Referring now specifically to FIG. 3D, it is seen that the flushable fluid handling assembly 100 is in a fourth operative orientation in which the handle element 170 of the flushable stopcock assembly 110 remains positioned so as to provide fluid communication along passageway 186 between only the second and third ports 166 and 168. The plunger 144 of the syringe 128 is now displaced, as indicated by an arrow 366, into a retracted position, thereby drawing blood from the patient into IV lines 312 and 338 as well as diluted blood into internal volume 178, the internal volume of the luer connector 192 and passageway 186. It is appreciated that handle element 170 has not been rotated from the orientation thereof shown in FIG. 3C. The operative orientation shown in FIG. 3D is particularly useful for drawing blood.

It is seen that handle element 324 of the blood sampling port assembly 310 remains positioned so as to provide fluid communication along passageway 352 between all of first, second and third ports 318, 320 and 322. It is seen that handle element 324 has not been rotated from the orientation thereof shown in FIG. 3C.

Figure 3E:
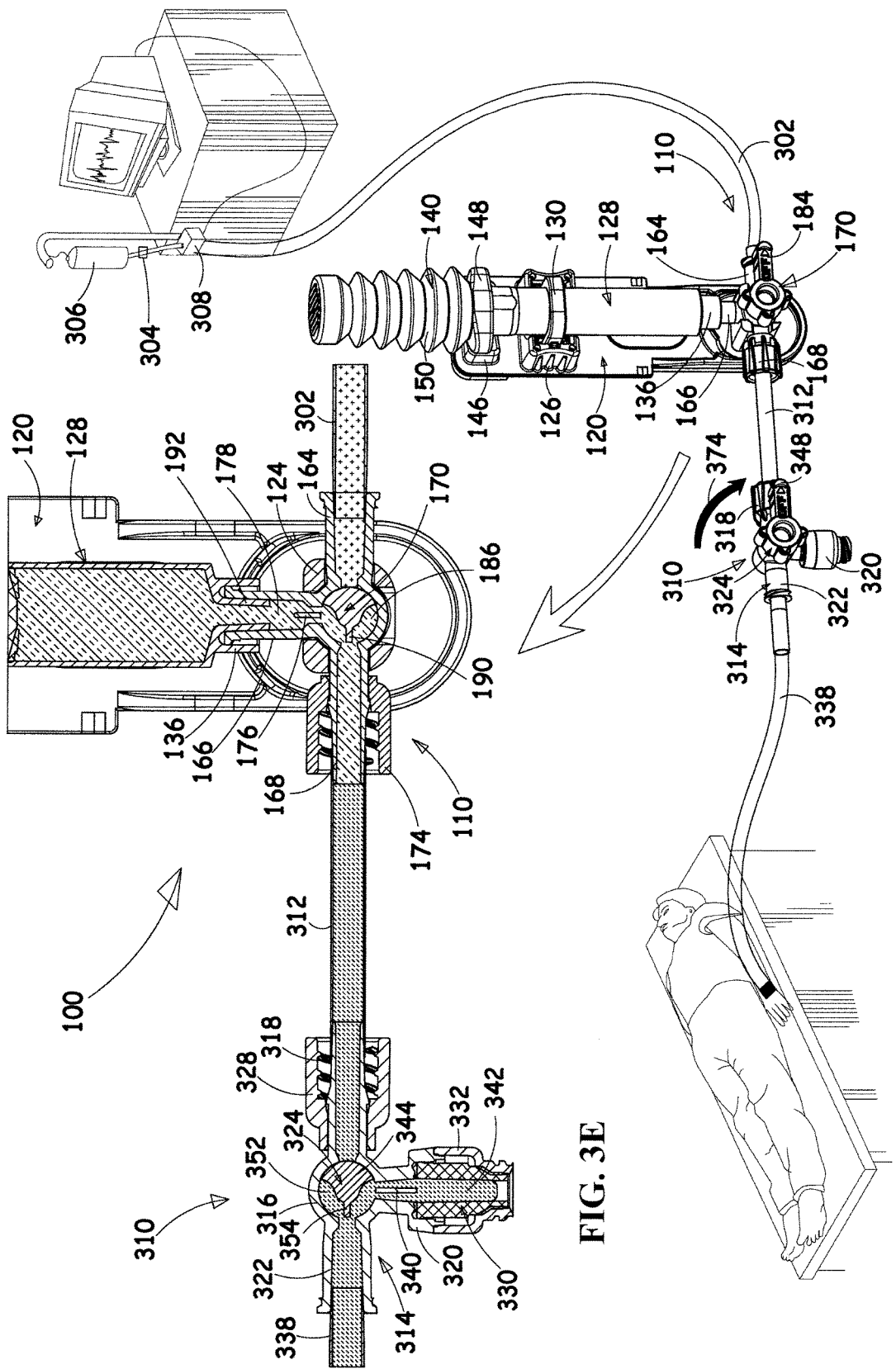

Referring now specifically to FIG. 3E, it is seen that the flushable fluid handling assembly 100 is in a fifth operative orientation in which the handle element 170 of the flushable stopcock assembly 110 remains positioned so as to provide fluid communication along passageway 186 between second and the third ports 166 and 168. The plunger 144 of the syringe 128 remains in a retracted position. It is appreciated that handle element 170 has not been rotated from the orientation thereof shown in FIG. 3D.

It is seen that handle element 324 of the blood sampling port assembly 310 is positioned so as to provide fluid communication along passageway 352 between only the second and third ports 320 and 322. It is seen that handle element 324 has been rotated clockwise, in the sense of FIGS. 3A-3K, as indicated by an arrow 374, by 90 degrees from the orientation thereof shown in FIGS. 3C and 3D. It is a particular feature of this embodiment of the present invention that blood, which may be diluted, in IV line 312 is isolated from port 320, thus preventing diluted blood from being sampled. The operative orientation shown in FIG. 3E is particularly useful just before sampling blood.

Figure 3F:
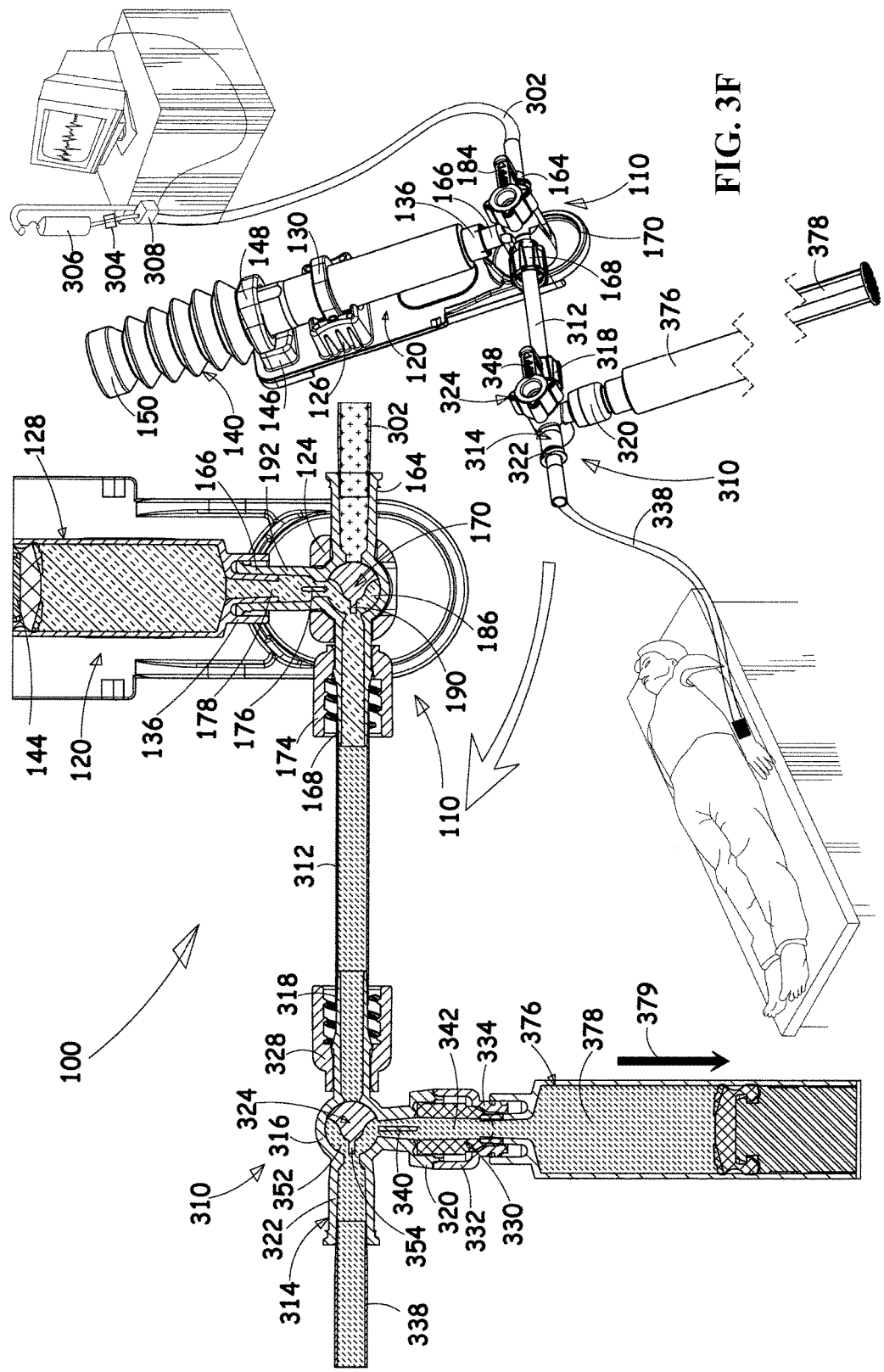

Referring now specifically to FIG. 3F, it is seen that the flushable fluid handling assembly 100 remains in the fifth operative orientation in which the handle element 170 of the flushable stopcock assembly 110 remains positioned so as to provide fluid communication along passageway 186 between only the second and third ports 166 and 168. The plunger 144 of the syringe 128 remains in a retracted position. It is appreciated that handle element 170 has not been rotated from the orientation thereof shown in FIG. 3E. What has changed is that a blood sampling syringe 376 has been inserted at the valve 330 of the blood sampling port assembly 310 and its piston 378 has been retracted, as indicated by an arrow 379, thereby drawing blood from the patient via IV line 338 into the interior of syringe 376. The orientation shown in FIG. 3F is particularly useful for sampling blood.

It is seen that handle element 324 of the blood sampling port assembly 310 remains positioned so as to provide fluid communication along passageway 352 between only the second and third ports 320 and 322. It is seen that handle element 324 has not been rotated from the orientation thereof shown in FIG. 3E.

Figure 3G:
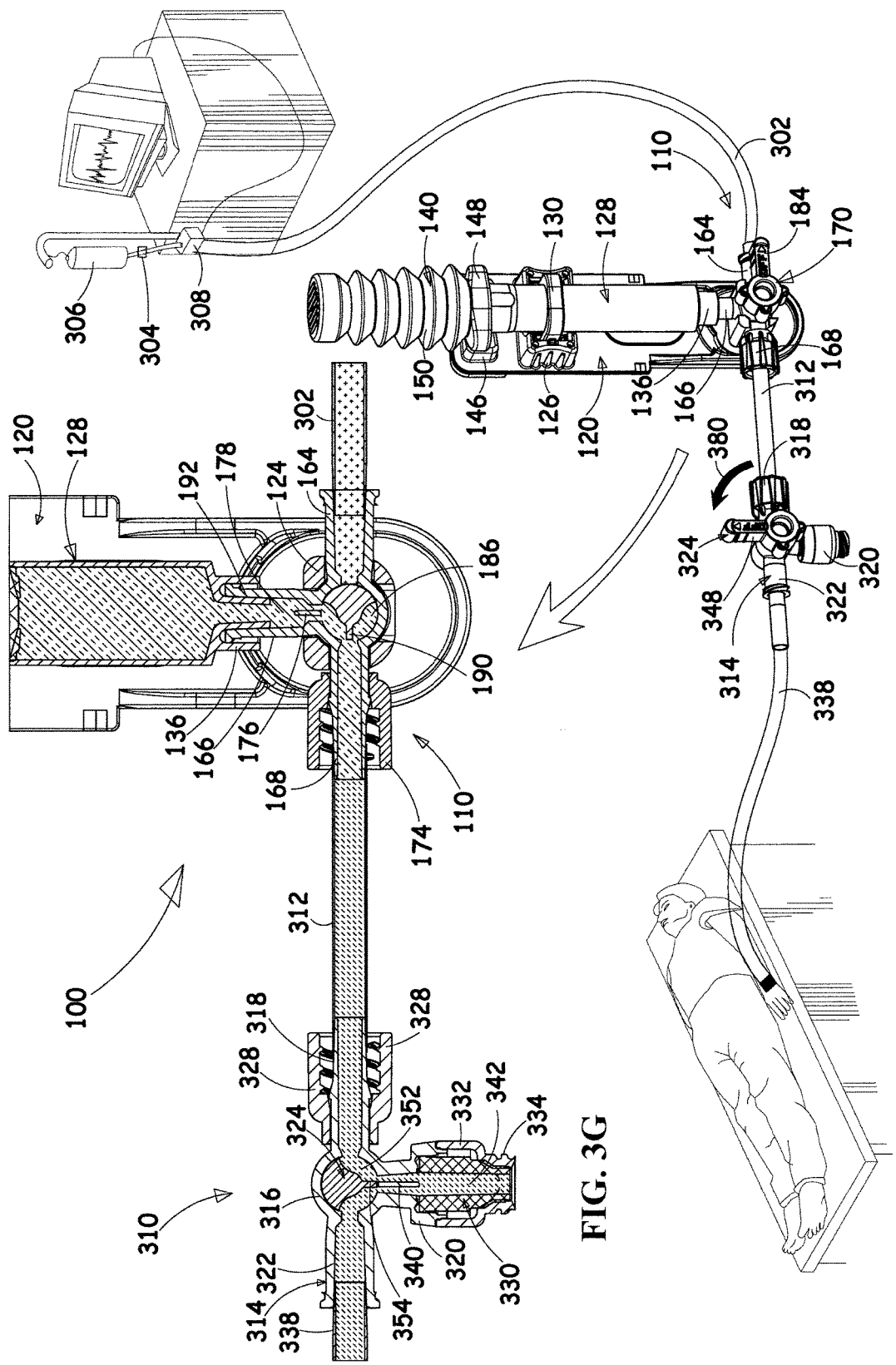

Referring now specifically to FIG. 3G, it is seen that the syringe 376 has been disengaged from the valve 330 and that flushable fluid handling assembly 100 is now in a sixth operative orientation in which the handle element 170 of the flushable stopcock assembly 110 remains positioned so as to provide fluid communication along passageway 186 between only the second and third ports 166 and 168. The plunger 144 of the syringe 128 remains in a retracted position. It is appreciated that handle element 170 has not been rotated from the orientation thereof shown in FIG. 3F.

It is seen that handle element 324 of the blood sampling port assembly 310 is positioned so as to provide fluid communication along passageway 352 between all of the first, second and third ports 318, 320 and 322. It is seen that handle element 324 has been rotated counterclockwise, in the sense of FIGS. 3A-3K, as indicated by an arrow 380, by 90 degrees from the orientation thereof shown in FIGS. 3E and 3F. Blood in IV line 338 is no longer isolated from IV line 312, from passageway 186, from internal volume 178 and from the internal volume of the luer connector 192. The orientation shown in FIG. 3G is particularly useful just before directing blood back to the patient from passageway 186, from internal volume 178 and the internal volume of the luer connector 192 and the remainder of the interior of the syringe 128.

Figure 3H:
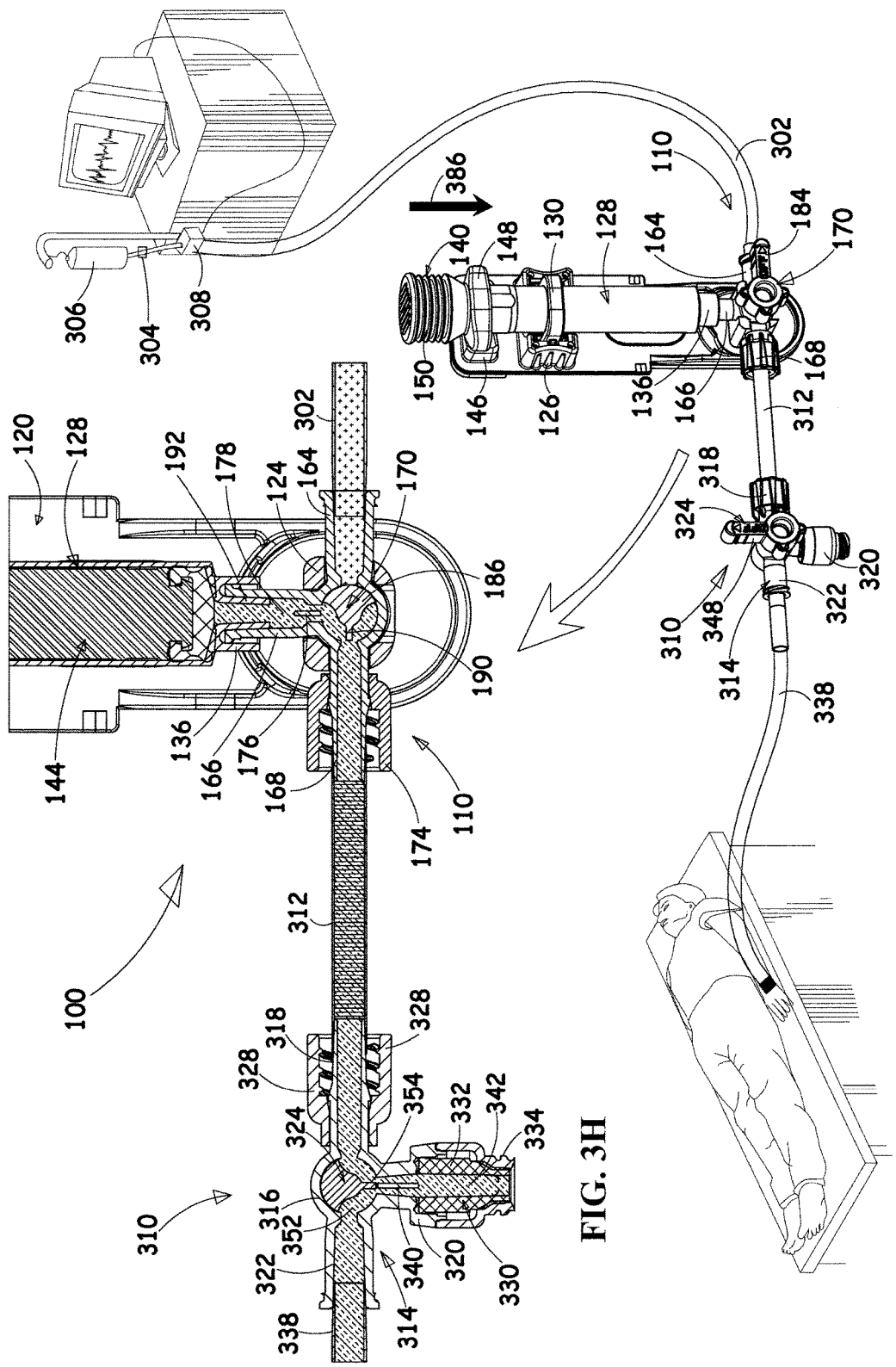

Referring now specifically to FIG. 3H, it is seen that the flushable fluid handling assembly 100 is now in a seventh operative orientation in which the handle element 170 of the flushable stopcock assembly 110 remains positioned so as to provide fluid communication along passageway 186 between only the second and third ports 166 and 168. The plunger 144 of the syringe 128 is displaced, as indicated by an arrow 386, to an extended position, thereby forcing diluted blood from the interior of the syringe 128, the internal volume of the luer connector 192, internal volume 178 and the passageway 186 out through the third port 168. It is appreciated that handle element 170 has not been rotated from the orientation thereof shown in FIG. 3G. The orientation shown in FIG. 3H is particularly useful for directing blood back to the patient from passageway 186, from internal volume 178 and the internal volume of the luer connector 192 and the remainder of the interior of the syringe 128 via the blood sampling port assembly 310 which remains in the same operative orientation as shown in FIG. 3G.

Figure 3I:
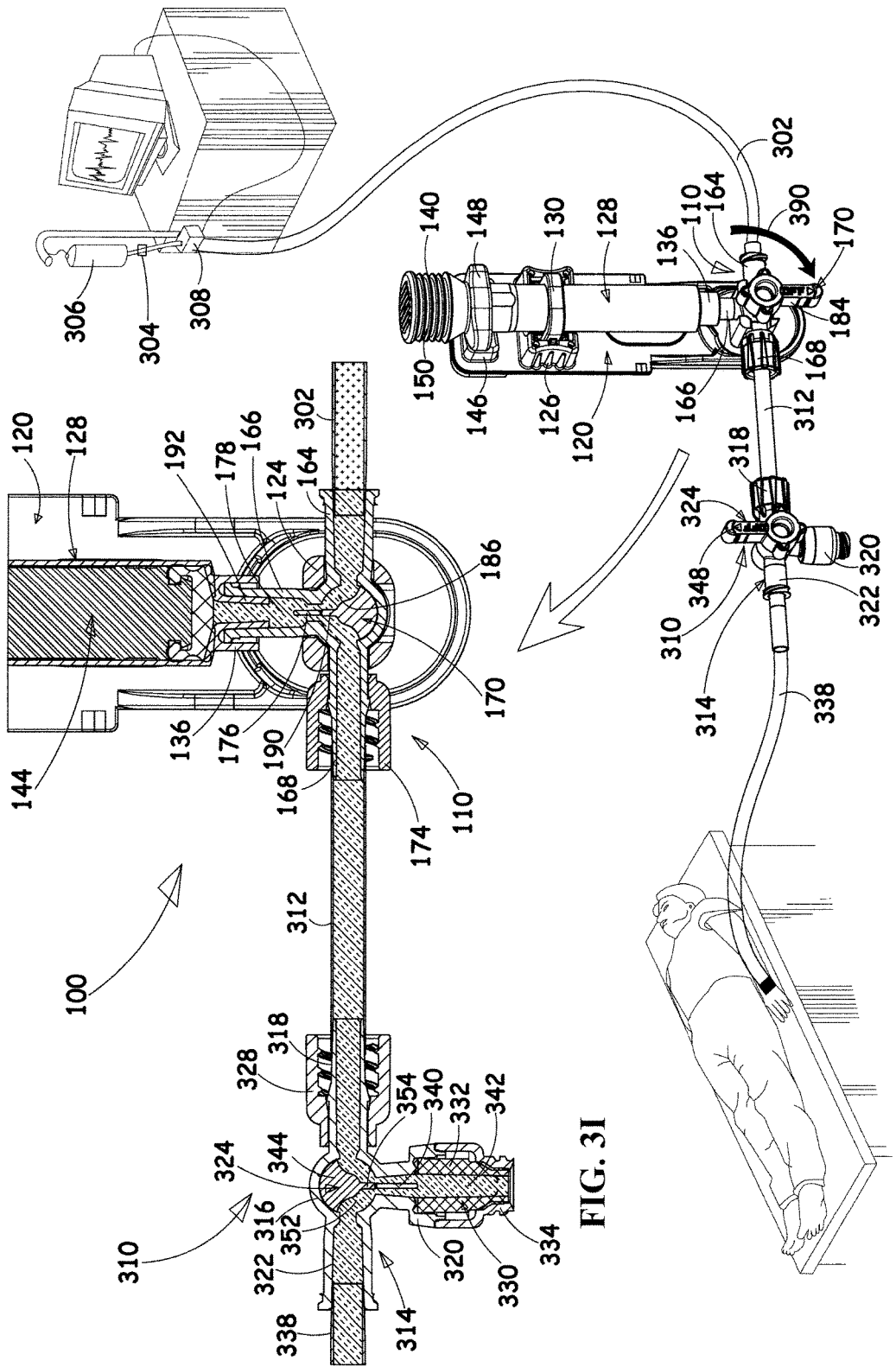

Referring now specifically to FIG. 3I, it is seen that the flushable fluid handling assembly 100 is now in an eighth operative orientation in which the handle element 170 of the flushable stopcock assembly 110 is positioned so as to provide fluid communication along passageway 186 between the first, second and third ports 164, 166 and 168. The plunger 146 of the syringe 128 remains in an extended position. It is appreciated that handle element 170 has been rotated clockwise, in the sense of FIGS. 3A-3K, as indicated by an arrow 390, by 90 degrees from the orientation thereof shown in FIG. 3H. The blood sampling port assembly 310 remains in the same operative orientation as shown in FIGS. 3G and 3H. The operative orientation shown in FIG. 3I is particularly useful just before flushing of internal volumes 178 and 342, the internal volume of the luer connector 192 and passageways 186 and 352.

Figure 3J:
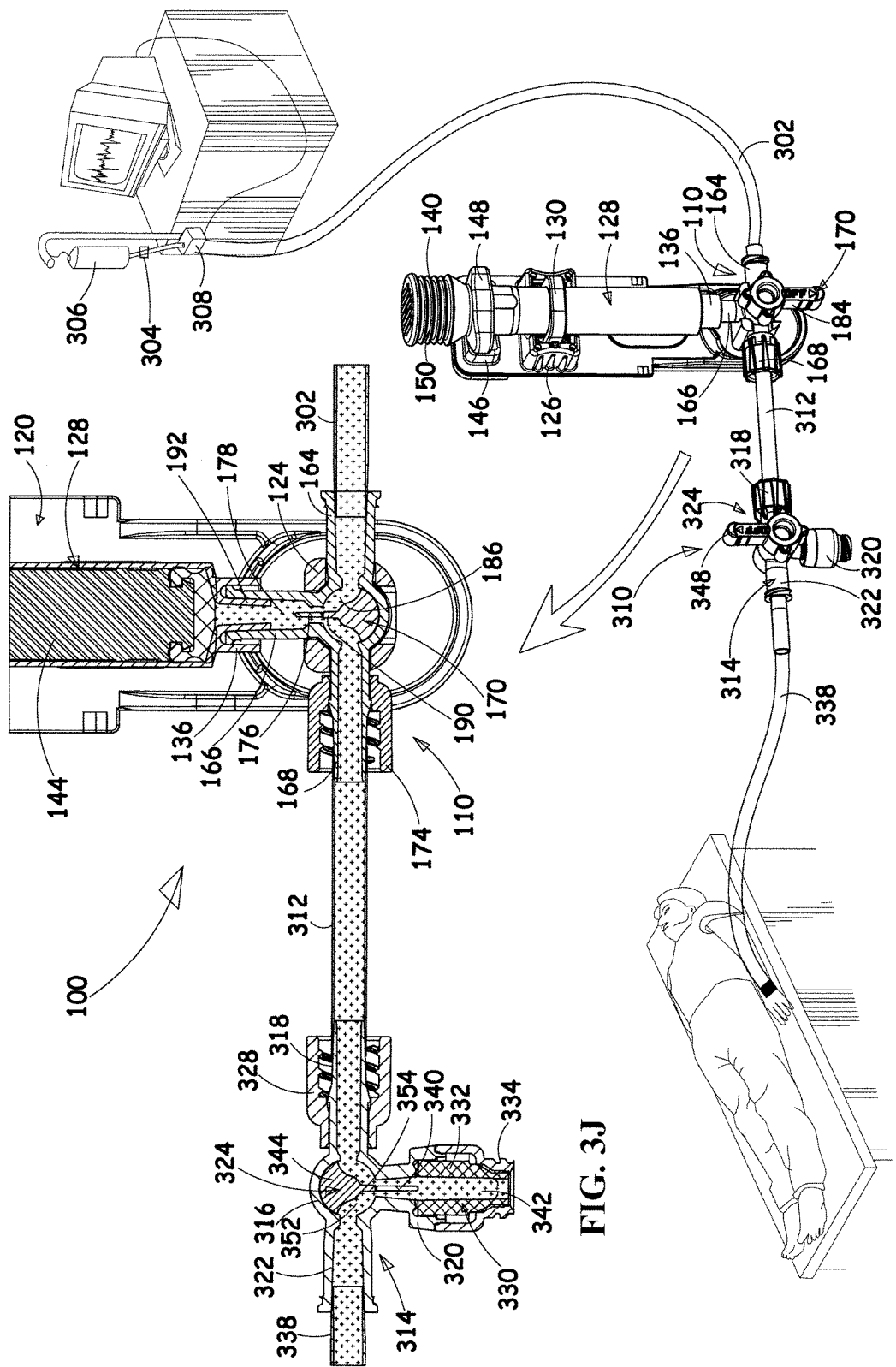

Referring now specifically to FIG. 3J, it is seen that the flushable fluid handling assembly 100 is now in a ninth operative orientation in which the handle element 170 of the flushable stopcock assembly 110 remains positioned so as to provide fluid communication along passageway 186 between the first, second and third ports 164, 166 and 168. The plunger 144 of the syringe 128 remains in an extended position. It is appreciated that handle element 170 has not been rotated from the orientation thereof shown in FIG. 3I. The blood sampling port assembly 310 remains in the same operative orientation as shown in FIGS. 3G, 3H and 3I. It is a particular feature of an embodiment of the present invention that sterile saline from bag 306 has flowed under gravity in response to operation of transducer 308 in a flushing mode and has flushed internal volume 178, the internal volume of the luer connector 192 and passageway 186 as sterile saline flowed past both fluid flow guide 176 and fluid flow guide 190, which are arranged along a single longitudinal axis in this operative orientation.

It is appreciated that in this operative orientation, a fluid flow of first fluid arriving from bag 306 via IV line 302 and first port 164 flows through fluid flow passageway 186 and does not flow entirely through said second port 166 whose internal volume is being flushed. This fluid flow of first fluid around fluid flow guides 176 and 190 enables flushing of any diluted blood that has remained in at least one of the internal volume of the luer connector 192, internal volume 178 and passageway 186.

The internal volume 342 of port 320 and the fluid flow passageway 352 are flushed as a result of fluid flow of sterile saline past both fluid flow guides 354 and 340, which are arranged along a single longitudinal axis in this operative orientation.

Figure 3K:
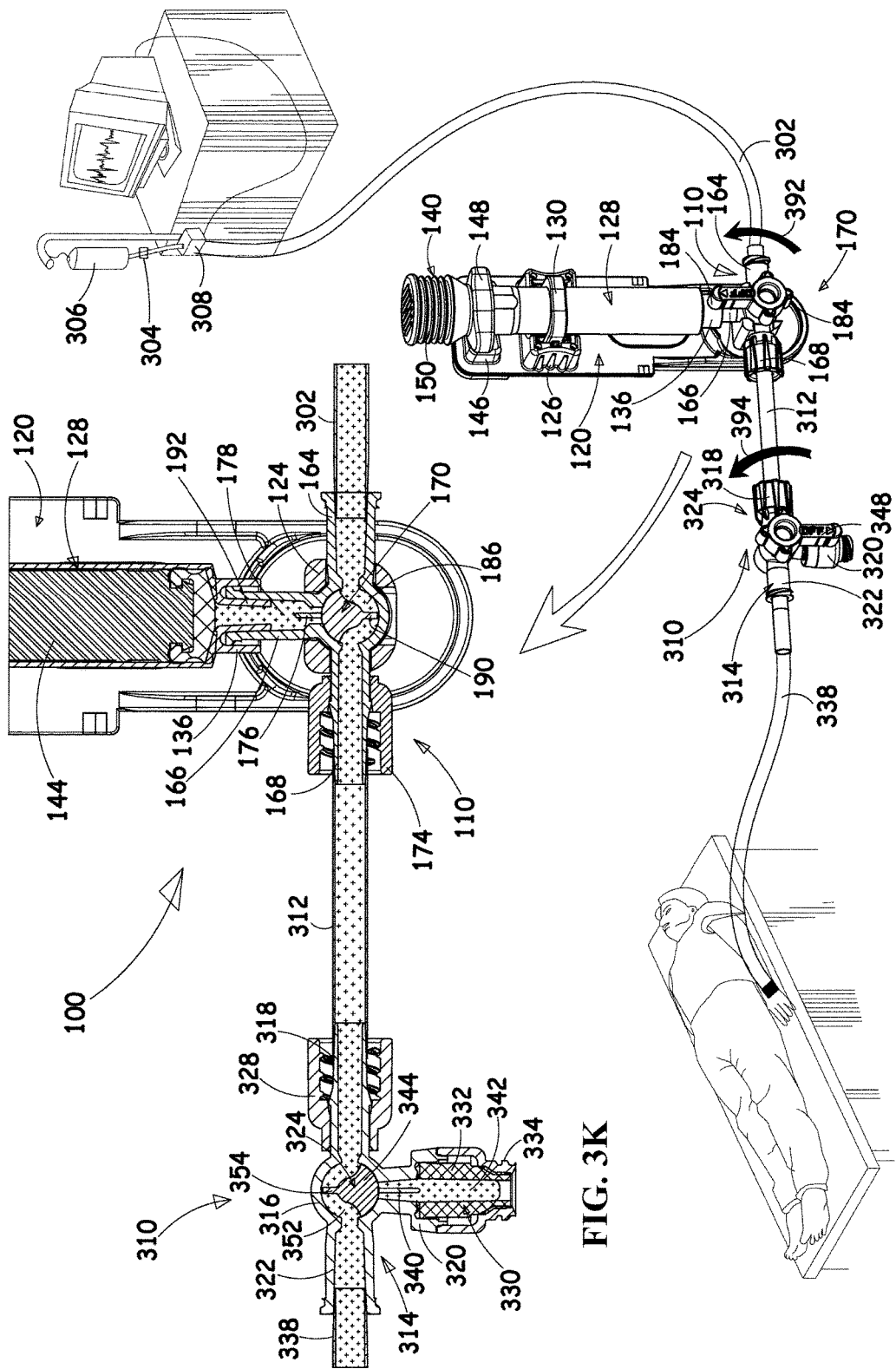

Referring now specifically to FIG. 3K, it is seen that the flushable fluid handling assembly 100 is now in a tenth operative orientation in which the handle element 170 of the flushable stopcock assembly 110 is positioned so as to provide fluid communication along passageway 186 between only the first and third ports 164 and 168. The plunger 146 of the syringe 128 remains in an extended position. It is appreciated that handle element 170 has been rotated counterclockwise, in the sense of FIGS. 3A-3K, as indicated by an arrow 392, by 180 degrees from the orientation thereof shown in FIG. 3J. It is seen that handle element 324 has been rotated counterclockwise, in the sense of FIGS. 3A-3K, as indicated by an arrow 394, by 180 degrees from the orientation thereof shown in FIGS. 3G, 3H and 3I. The flushable fluid handling assembly 100 is in an operative orientation suitable for blood pressure monitoring by transducer 308.

It will be appreciated by persons skilled in the art that the present invention is not limited to what has been particularly described hereinabove and includes both combinations and subcombinations of features described hereinabove as well as variations and modifications thereof which would occur to persons skilled in the art upon reading the foregoing and which are not in the prior art.

The invention claimed is:

1. A flushable fluid handling assembly comprising:
a housing element defining a central bore and at least first, second and third ports, said first and third ports being line connection ports and said second port being a syringe connection port;
a handle element which is selectably positionable relative to said housing element;
at least one fluid passageway communicating between at least two of said at least first, second and third ports, said at least one fluid passageway being selectably defined by rotational positioning of said handle element relative to said housing element;
a first fluid flow guide extending radially to an inner facing wall of said central bore, said first fluid flow guide associated with said at least one fluid flow passageway, and
a syringe fixedly connected to said second port, said syringe including an axially displaceable plunger;
and wherein said handle element and said syringe are positionable in all of the following operative orientations:
a first operative orientation in which said handle element is positioned so as to provide fluid communication along at least part of said at least one fluid passageway between said first, second and third ports and said plunger of said syringe is in an extended position and said passageway is filled with a first fluid;
a second operative orientation in which said handle element is positioned so as to provide fluid communication along at least part of said at least one fluid passageway only between said first and third ports;
a third operative orientation in which said handle element is positioned so as to provide fluid communication along at least part of said at least one fluid passageway between said second and third ports;
a fourth operative orientation in which said handle element is positioned so as to provide fluid communication along at least part of said at least one fluid passageway between said second and third ports and said plunger of said syringe is in a retracted position, thereby drawing a second fluid via said third port into at least part of said passageway, said second port and said syringe;
a fifth operative orientation in which said handle element is positioned so as to provide fluid communication along at least part of said at least one fluid passageway between said first and second ports but not with the third port and said plunger remains retracted, thereby preventing said first fluid from passing through said third port;
a sixth operative orientation in which said handle element is positioned so as to provide fluid communication along at least part of said at least one fluid passageway between said second and third ports and said plunger is extended, thereby forcing said second fluid out of said syringe, said internal volume and said at least one fluid passageway via said third port;
a seventh operative orientation in which said handle element is positioned so as to provide fluid communication along at least part of said at least one fluid passageway between said first, second and third ports and said plunger of said syringe is in a retracted position;
an eighth operative orientation in which said handle element is positioned so as to provide fluid communication along at least part of said at least one fluid passageway between said first, second and third ports and said plunger is extended, thereby flushing said second fluid from said second port and said at least one fluid passageway.

2. A flushable fluid handling assembly according to claim 1 and also comprising a second fluid flow guide extending radially and partially bifurcating said second port, said second fluid flow guide being associated with said at least one fluid flow passageway.

3. A flushable fluid handling assembly according to claim 1 and wherein said syringe has a luer connector having an interior volume and said second port is sealingly threadably connected to said luer connector.

4. A flushable fluid handling assembly according to claim 3 and wherein said at least one fluid passageway is configured for enabling flushing of at least one of said interior volume of said luer connector and said second port by a fluid flow which does not flow entirely through said second port whose internal volume is being flushed.

5. A flushable fluid handling assembly according to claim 2 and wherein said syringe has a luer connector having an interior volume and said second port is sealingly threadably connected to said luer connector.

6. A flushable fluid handling assembly according to claim 2 and wherein said first fluid flow guide and said second fluid flow guide are configured to be selectively arranged along a single axis for enabling flushing of at least one of said interior volume and said second port.

7. A flushable fluid handling assembly according to claim 3 and wherein:
said handle element and said housing element are arrangeable in multiple mutual positions; and
said first fluid flow guide and said at least one fluid passageway are configured for enabling flushing at least one of said second port and said interior volume by a fluid flow which does not flow entirely through said second port whose internal volume is being flushed when said housing element and said handle element are in at least one of said multiple mutual positions.

8. A flushable fluid handling assembly according to claim 5 and wherein:
said handle element and said housing element are arrangeable in multiple mutual positions; and
said first fluid flow guide, said second fluid flow guide, which is selectively arranged along a single axis with said first fluid flow guide, and said at least one fluid passageway are configured for enabling flushing at least one of said second port and said interior volume by a fluid flow which does not flow entirely through said second port whose internal volume is being flushed when said housing element and said handle element are in at least one of said multiple mutual positions.

9. A flushable fluid handling assembly according to claim 1 and wherein said syringe is adapted for use in a blood sampling procedure.

10. A flushable fluid handling assembly according to claim 9 and wherein said syringe is adapted to serve as a container for diluted blood being present in said flushable fluid handling assembly as part of said blood sampling procedure.

11. A flushable fluid handling assembly according to claim 1 and also comprising a mounting base and wherein said syringe is snap-fit mounted onto said mounting base.

12. A flushable fluid handling assembly according to claim 11 and wherein said housing element is snap-fit mounted onto said mounting base.

13. A flushable fluid handling assembly according to claim 1 and wherein said first fluid is saline and said second fluid is a diluted blood.

14. A flushable fluid handling assembly according to claim 13 and wherein at least one of said operative orientations is useful for at least one of the following operations:
   priming of said flushable fluid handling assembly;
   blood pressure monitoring via a blood pressure transducer forming part of the flushable fluid handling assembly;
   drawing a blood sample from a patient causing said diluted blood to be drawn into said syringe;
   isolating said blood sample from said at least one fluid passageway and from said syringe;
   sampling blood from said flushable fluid handling assembly;
   directing said blood sample and said diluted blood back to the patient from said fluid passageway and from said syringe; and
   flushing of said second port, said at least one fluid passageway and said syringe.

15. A method of blood sampling using a flushable fluid handling assembly, comprising the steps of:
   providing a stopcock fixedly connected to a syringe having a displaceable plunger and a luer connector defining an interior volume; said stopcock being adapted to be fluidly coupled to an IV line, which is connected to an IV bag containing a first fluid, said stopcock including a housing element, a handle element, at least one fluid flow passageway defined by relative arrangement between said housing element and said handle element and a fluid flow guide associated with said fluid flow passageway;
   providing a sampling port, fluidly coupled to said IV line, to said stopcock and to a patient circulatory system and located between said stopcock and said patient;
   filling said IV line with said first fluid;
   drawing a second fluid from said patient into at least part of said IV line, by displacing said displaceable plunger of said syringe;
   sampling said second fluid using said sampling port;
   directing said second fluid back into the patient, by displacing said displaceable plunger of said syringe; and
   flushing said interior volume of said luer connector by a fluid flow of said first fluid flowing past said fluid flow guide.

16. A method of blood sampling using a flushable fluid handling assembly according to claim 15 and wherein:
   said housing element defines a central bore and at least first, second and third ports, said first and third ports being line connection ports and said second port being a syringe connection port;
   said handle element is selectably positionable relative to said housing element;
   said fluid flow passageway communicates between at least two of said at least first, second and third ports, said at least one fluid flow passageway being selectably defined by rotational positioning of said handle element relative to said housing element; and
   said first fluid flow guide extends radially to an inner facing wall of said central bore, said first fluid flow guide associated with said at least one fluid flow passageway.

17. A method of blood sampling using a flushable fluid handling assembly according to claim 16 and wherein said stopcock also includes a second fluid flow guide extending radially and partially bifurcating said second port, said second fluid flow guide being associated with said at least one fluid flow passageway.

18. A method of blood sampling using a flushable fluid handling assembly according to claim 16 and wherein said second port is sealingly threadably connected to said luer connector of said syringe.

19. A method of blood sampling using a flushable fluid handling assembly according to claim 16 and wherein said at least one fluid passageway is configured for enabling flushing at least one of said interior volume of said luer connector and said second port by a fluid flow which does not flow entirely through said second port whose internal volume is being flushed.

20. A method of blood sampling using a flushable fluid handling assembly according to claim 17 and wherein said first fluid flow guide and said second fluid flow guide are configured to be selectively arranged along a single axis for enabling flushing of at least one of said interior volume and said second port.

21. A method of blood sampling using a flushable fluid handling assembly according to claim 15 and wherein:
   said handle element and said housing element are arrangeable in multiple mutual positions; and
   said first fluid flow guide and said at least one fluid passageway are configured for enabling flushing of at least one of said second port and said interior volume by a fluid flow which does not flow entirely through said second port whose internal volume is being flushed when said housing element and said handle element are in at least one of said multiple mutual positions.

22. A method of blood sampling using a flushable fluid handling assembly according to claim 17 and wherein:
   said handle element and said housing element are arrangeable in multiple mutual positions; and
   said first fluid flow guide, said second fluid flow guide, which is selectively arranged along a single axis with said first fluid flow guide, and said at least one fluid passageway are configured for enabling flushing at least one of said second port and said interior volume by a fluid flow which does not flow entirely through said second port whose internal volume is being flushed when said housing element and said handle element are in at least one of said multiple mutual positions.

23. A method of blood sampling using a flushable fluid handling assembly according to claim 15 and wherein:
   said providing also comprises providing a mounting base; and
   said syringe is snap-fit mounted onto said mounting base.

24. A method of blood sampling using a flushable fluid handling assembly according to claim 23 and wherein said housing element is snap-fit mounted onto said mounting base.

25. A method of blood sampling using a flushable fluid handling assembly according to claim 15 and wherein said handle element and said first syringe are positionable in at least one of the following operative orientations:
- a first operative orientation in which said handle element is positioned so as to provide fluid communication along at least part of said at least one fluid passageway between said first, second and third ports and said first plunger of said first syringe is in an extended position and said passageway is filled with a first fluid;
- a second operative orientation in which said handle element is positioned so as to provide fluid communication along at least part of said at least one fluid passageway only between said first and third ports;
- a third operative orientation in which said handle element is positioned so as to provide fluid communication along at least part of said at least one fluid passageway between said second and third ports;
- a fourth operative orientation in which said handle element is positioned so as to provide fluid communication along at least part of said at least one fluid passageway between said second and third ports and said first plunger of said first syringe is in a retracted position, thereby drawing a second fluid via said third port into at least part of said passageway, said second port and said syringe;
- a fifth operative orientation in which said handle element is positioned so as to provide fluid communication along at least part of said at least one fluid passageway between said first and second ports but not with the third port and said first plunger remains retracted, thereby preventing said first fluid from passing through said third port;
- a sixth operative orientation in which said handle element is positioned so as to provide fluid communication along at least part of said at least one fluid passageway between said second and third ports and said first plunger is extended, thereby forcing said second fluid out of said syringe, said internal volume and said at least one fluid passageway via said third port;
- a seventh operative orientation in which said handle element is positioned so as to provide fluid communication along at least part of said at least one fluid passageway between said first, second and third ports and said plunger of said syringe is in a retracted position; and
- an eighth operative orientation in which said handle element is positioned so as to provide fluid communication along at least part of said at least one fluid passageway between said first, second and third ports and said first plunger is extended, thereby flushing said second fluid from said second port and said at least one fluid passageway.

26. A method of blood sampling using a flushable fluid handling assembly according to claim 25 and wherein said first fluid is saline and said second fluid is a diluted blood.

27. A method of blood sampling using a flushable fluid handling assembly according to claim 25 and wherein at least one of said operative orientations is useful for at least one of the following operations:
- priming of said flushable fluid handling assembly;
- blood pressure monitoring via a blood pressure transducer forming part of the flushable fluid handling assembly;
- drawing a blood sample from a patient causing said diluted blood to be drawn into said syringe;
- isolating said blood sample from said at least one fluid passageway and from said syringe;
- sampling blood from said flushable fluid handling assembly;
- directing said blood sample and said diluted blood back to the patient from said fluid passageway and from said syringe; and
- flushing of said second port, said at least one fluid passageway and said syringe.

28. A method of blood sampling using a flushable fluid handling assembly according to claim 26 and wherein said syringe is adapted to serve as a container for said diluted blood being present in said flushable fluid handling assembly as part of said blood sampling procedure.

* * * * *